United States Patent
Zagar et al.

[11] Patent Number: 6,100,218
[45] Date of Patent: Aug. 8, 2000

[54] SUBSTITUTED 2-PHENYLPYRIDINES

[75] Inventors: Cyrill Zagar, Ludwigshafen; Peter Schäfer, Ottersheim; Gerhard Hamprecht, Weinheim; Elisabeth Heistracher; Markus Menges, both of Mannheim; Olaf Menke, Altleiningen; Karl-Otto Westphalen, Speyer; Ulf Misslitz, Neustadt; Helmut Walter, Obrigheim, all of Germany

[73] Assignee: BASF Aktiengesellschaft, Ludwigshafen, Germany

[21] Appl. No.: 09/117,655

[22] PCT Filed: Feb. 17, 1997

[86] PCT No.: PCT/EP97/00735

§ 371 Date: Aug. 4, 1998

§ 102(e) Date: Aug. 4, 1998

[87] PCT Pub. No.: WO97/30059

PCT Pub. Date: Aug. 21, 1997

[30] Foreign Application Priority Data

Feb. 16, 1996 [DE] Germany ............... 196 05 766

[51] Int. Cl.[7] ............... A01N 57/08; C07F 9/58
[52] U.S. Cl. ............ 504/128; 546/22; 504/116; 504/127; 504/195; 504/244
[58] Field of Search ............... 504/116, 127, 504/128, 130, 195, 244; 546/22

[56] References Cited

U.S. PATENT DOCUMENTS

| | | | |
|---|---|---|---|
| 4,560,752 | 12/1985 | Lee | 544/66 |
| 4,859,229 | 8/1989 | Wenger et al. | 71/92 |
| 5,151,357 | 9/1992 | Koide et al. | 430/610 |
| 5,189,030 | 2/1993 | Maier | 514/114 |
| 5,294,639 | 3/1994 | Kirstgen et al. | 514/522 |
| 5,409,954 | 4/1995 | Kirstgen et al. | 514/522 |
| 5,418,233 | 5/1995 | Linz et al. | 514/247 |
| 5,434,288 | 7/1995 | Lennon | 558/182 |
| 5,463,071 | 10/1995 | Himmelsbach et al. | 548/251 |
| 5,563,268 | 10/1996 | Linz et al. | 544/238 |
| 5,783,522 | 7/1998 | Schaefer et al. | 504/294 |

FOREIGN PATENT DOCUMENTS

| | | |
|---|---|---|
| 2199846 | 9/1995 | Canada . |
| 078536 | 5/1983 | European Pat. Off. . |
| 421436 | 4/1991 | European Pat. Off. . |
| 544587 | 6/1993 | European Pat. Off. . |
| 563384 | 10/1993 | European Pat. Off. . |
| 2729142 | 7/1996 | France . |
| 3737152 | 11/1987 | Germany . |
| 4029444 | 9/1989 | Germany . |
| 40 29 444 | 9/1990 | Germany . |
| 4121959 | 6/1991 | Germany . |
| 4431219 | 9/1994 | Germany . |
| 4437197 | 10/1994 | Germany . |
| 5178810 | 9/1991 | Japan . |
| 2263109 | 7/1993 | United Kingdom . |
| 95/02580 | 1/1995 | WIPO . |
| 95/35281 | 12/1995 | WIPO . |
| 96/15115 | 5/1996 | WIPO . |

OTHER PUBLICATIONS

Theodoridis et al., *ACS Symp. Ser.*, 584, pp. 90–99, 1995.
*Chem. Abst.*, vol. 115, 1991, AN 207989t (plus full translation of JP–A 03/151367, Jun. 27, 1991).
Maier et al., *Sulfur Silicon Relat. Elem.*, vol. 107, 1995, pp. 245–255.
*Org. Reactions*, vol. 11, Chapter 3, pp. 189–260 (1960).
*Chem. Abst.*, vol. 62, 1965, AN 13177 f/g.
Theodoridis et al., *ACS Symp. Ser.*, 584, 1995, pp. 90–99.

*Primary Examiner*—John Kight
*Assistant Examiner*—Charanjit S. Aulakh
*Attorney, Agent, or Firm*—Keil & Weinkauf

[57] ABSTRACT

2-Phenylpyridines I

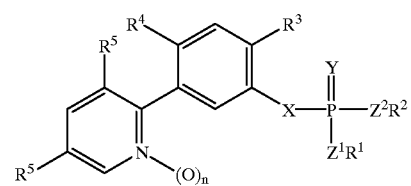

wherein

X is a chemical bond, 1,2-ethynediyl or optionally substituted $-(CH_2)_{1-3}-$, $-O-(CH_2)_{1-2}-$, $-S-(CH_2)_{1-2}-$, $-CH_2-O-CH_2-$, $-CH_2-S-CH_2-$ or $-CH=CH-$;

Y is oxygen or sulfur;

$Z^1$ is oxygen, sulfur or $-N(R^7)-$;

$Z^2$ is oxygen, sulfur or $-N(R^8)-$;

$R^1$, $R^2$, $R^7$ and $R^8$ independently of one another are hydrogen, optionally substituted alkyl, alkenyl, alkynyl, cycloalkyl, phenyl or heterocyclyl; or $R^1$ and $R^2$ or $R^7$, or $R^2$ and $R^8$ together are optionally substituted $-(CH_2)_{2-5}-$ or $-(CH_2)_2-O-(CH_2)_2-$, or $R^1$ and $R^2$ together are optionally substituted 1,2-phenylene;

$R^3$ is cyano, halogen, alkyl, haloalkyl, alkoxy or haloalkoxy;

$R^4$ and $R^5$ are hydrogen or halogen;

$R^6$ is halogen or haloalkyl;

n is zero or one;

and their salts are suitable for controlling undesirable vegetation and as desiccants or defoliants.

20 Claims, No Drawings

SUBSTITUTED 2-PHENYLPYRIDINES

This application is a 371 of PCT/EP97/00735 filed Feb. 17, 1997, now WO 97/30059 Aug. 21, 1997.

The present invention relates to novel substituted 2-phenylpyridines of the formula I

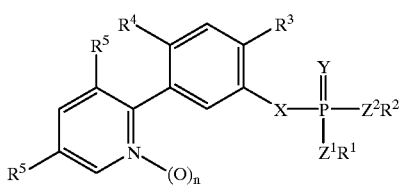

where the variables have the following meanings:

X is a chemical bond, 1,2-ethynediyl or
  a methylene, 1,2-ethanediyl or 1,3-propylene bridge, which, if desired, can have attached to it a hydroxyl, amino or $C_1$–$C_4$-alkylamino substituent;
  methyleneoxymethylene, methylenethiamethylene, ethene-1,2-diyl or
  oxymethylene, thiamethylene, oxyethylene or thiaethylene, bonded to the phenyl ring via the hetero atom, it being possible, if desired, for the last two chains to have a hydroxyl, amino or $C_1$–$C_4$-alkylamino group attached to the carbon atom adjacent to the phosphorous;
and it being possible for each of the last-mentioned 10 bridges to have attached to it one or two of the following substituents: cyano, carboxyl, halogen, $C_1$–$C_4$-alkyl, $C_1$–$C_4$-haloalkyl, $C_1$–$C_4$-alkoxy, $C_1$–$C_4$-haloalkoxy, ($C_1$–$C_4$-alkoxy)carbonyl and/or di-($C_1$–$C_4$-alkyl)amino;

Y is oxygen or sulfur;
$Z^1$ is oxygen, sulfur or —N($R^7$)—;
$Z^2$ is oxygen, sulfur or —N($R^8$)—;
$R^1$, $R^2$, $R^7$ and $R^8$ independently of one another are hydrogen, $C_1$–$C_6$-alkyl, $C_1$–$C_6$-haloalkyl, hydroxy-$C_1$–$C_4$-alkyl, cyano-$C_1$–$C_4$-alkyl, $C_1$–$C_4$-alkoxy-$C_1$–$C_4$-alkyl, $C_1$–$C_4$-haloalkoxy-$C_1$–$C_4$-alkyl, $C_3$–$C_4$-alkenyloxy-$C_1$–$C_4$-alkyl, $C_3$–$C_4$-alkynyloxy-$C_1$–$C_4$-alkyl, $C_3$–$C_8$-cycloalkoxy-$C_1$–$C_4$-alkyl, amino-$C_1$–$C_4$-alkyl, $C_1$–$C_4$-alkylamino-$C_1$–$C_4$alkyl, di($C_1$–$C_4$-alkyl)amino-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_3$–$C_4$-alkenylthio-$C_1$–$C_4$-alkyl, $C_3$–$C_4$-alkynylthio-$C_1$–$C_4$-alkyl, $C_1$–$C_4$-alkylsulfinyl-$C_1$–$C_4$-alkyl, $C_1$–$C_4$-haloalkylsulfinyl-$C_1$–$C_4$-alkyl, $C_3$–$C_3$-alkenylsulfinyl-$C_1$–$C_4$-alkyl, $C_3$–$C_4$-alkynylsulfinyl-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, $C_3$–$C_4$-alkenylsulfonyl-$C_1$–$C_4$-alkyl, $C_3$–$C_4$-alkynylsulfonyl-$C_1$–$C_4$-alkyl, $C_3$–$C_6$-alkenyl, $C_3$–$C_6$-haloalkenyl, cyano-$C_3$–$C_6$-alkenyl, $C_3$–$C_6$-alkynyl, $C_3$–$C_6$-haloalkynyl, cyano-$C_3$–$C_6$-alkynyl, hydroxycarbonyl-$C_1$–$C_4$-alkyl, ($C_1$–$C_4$-alkoxy)carbonyl-$C_1$–$C_4$-alkyl, ($C_1$–$C_4$-alkylthio)carbonyl-$C_1$–$C_4$-alkyl, aminocarbonyl-$C_1$–$C_4$-alkyl, ($C_1$–$C_4$-alkyl)aminocarbonyl-$C_1$–$C_4$-alkyl, di($C_1$–$C_4$-alkyl)aminocarbonyl-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl or 3- to 7-membered heterocyclyl or heterocyclyl-$C_1$–$C_4$-alkyl, it being possible, if desired, for all heterocycles to contain a carbonyl or thiocarbonyl ring member, and it being possible for all cycloalkyl, phenyl and heterocyclyl rings to be unsubstituted or to have attached to them one to four substituents, in each case selected from the group consisting of halogen, cyano, nitro, amino, hydroxyl, carboxyl, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkyl)carbonyl, ($C_1$–$C_4$-haloalkyl)carbonyl, ($C_1$–$C_4$-alkoxy) carbonyl, ($C_1$–$C_4$-alkyl)carbonyloxy, ($C_1$–$C_4$-haloalkyl)carbonyloxy and di($C_1$–$C_4$-alkyl)amino, or $R^1$ and $R^2$ or $R^1$ and $R^7$ and/or $R^2$ and $R^8$ in each case together form a 1,2-ethanediyl, 1,3-propylene, tetramethylene, pentamethylene or ethyleneoxyethylene chain which, if desired, can be substituted by one to four $C_1$–$C_4$-alkyl and/or one or two ($C_1$–$C_4$-alkoxy)carbonyl groups, or $R^1$ and $R^2$ together are 1,2-phenylene which can be unsubstituted or have attached to it one to three substituents, in each case selected from the group consisting of cyano, nitro, halogen, $C_1$–$C_4$-alkyl, $C_1$–$C_4$-haloalkyl, $C_1$–$C_4$-alkoxy and $C_1$–$C_4$-haloalkoxy;

$R^3$ is cyano, halogen, $C_1$–$C_4$-alkyl, $C_1$–$C_4$-haloalkyl, $C_1$–$C_4$-alkoxy or $C_1$–$C_4$-haloalkoxy;

$R^4$, $R^5$ in each case are hydrogen or halogen;

$R^6$ is halogen or $C_1$–$C_4$-haloalkyl;

n is zero or one;

and to the agriculturally useful salts of the compounds I.

Furthermore, the invention relates to
  the use of the compounds I as herbicides or for the desiccation/defoliation of plants,
  herbicidal compositions and compositions for the desiccation/defoliation of plants which comprise the compounds I as active substances,
  processes for the preparation of the compounds I and of herbicidal compositions and compositions for the desiccation/defoliation of plants which make use of the compounds I, and
  methods of controlling undesirable vegetation and for the desiccation/defoliation of plants using the compounds I.

U.S. Pat. No. 5,434,288 describes certain benzene derivatives as phospholipase A2 inhibitors. The broad definition of these compounds also includes some of the present substituted 2-phenylpyridines I if the suitable substituents are selected.

Furthermore, some of the compounds I—when suitable substituents are chosen—come under the general formulae of
  platelet-activating factor (PAF) antagonists described in GB-A 2 263 109;
  supported catalysts for the production of acetic acid which are described in DE-A 41 21 959;
  antithrombic, antiaggregatory and tumor-inhibitor reactive substances described in EP-A 537 696;
  intermediates for the preparation of certain NMDA receptor inhibitors, mentioned in EP-A 421 436;
  intermediates for the preparation of certain insecticides, mentioned in EP-A 544 587;
  intermediates for the preparation of certain PDE IV inhibitors, mentioned in WO 95/35281;
  intermediates for the preparation of asymmetric 9-cyanostyryl-10-styrylanthracene derivatives, mentioned in JP-A 05/178 810;
  intermediates for the preparation of certain insecticides, acaricides, nematicides and fungicides, mentioned in EP-A 474 042.

2-Phenylpyridines as herbicides or for the desiccation/defoliation of plants have already been taught in WO 95/02580.

However, the herbicidal properties of the prior-art 2-phenylpyridines with regard to the harmful plants are not always entirely satisfactory.

It is an object of the present invention to provide novel herbicidally active 2-phenylpyridines which allow better targeted control of undesirable plants than has been possible to date. The object also extends to the provision of novel compounds which act as desiccants/defoliants.

We have found that this object is achieved by the present substituted 2-phenylpyridines of the formula I and by their herbicidal activity.

Furthermore, there have been found herbicidal compositions which comprise the compounds I and which have a very good herbicidal activity. Moreover, there have been found processes for the preparation of these compositions and methods of controlling undesirable vegetation using the compounds I.

In addition, we have found that the compounds I are also suitable for the desiccation/defoliation of parts of plants, suitable plants being crop plants such as cotton, potatoes, oilseed rape, sunflowers, soybeans or field beans, in particular cotton. Thus, we have found compositions for the desiccation and/or defoliation of plants, processes for the preparation of these compositions and methods for the desiccation and/or defoliation of plants using the compounds I.

Depending on the substitution pattern, the compounds of the formula I can contain one or more chiral centers, in which case they are present in the form of enantiomer or diastereomer mixtures. E/Z isomers are also possible, depending on the meaning of X. The invention relates both to the pure enantiomers or diasteromers and to mixtures of these.

Agriculturally useful salts are to be understood mainly as the salts of I with those cations, and acid addition salts of I with those acids, which do not adversely affect the herbicidal or desiccation/defoliant action of I.

Thus, suitable cations are, in particular, the ions of the alkali metals, preferably sodium and potassium, of the alkaline earth metals, preferably calcium, magnesium and barium, and of the transition metals, preferably manganese, copper, zinc and iron, and the ammonium ion, which can have attached to it a $C_1$–$C_4$-alkyl, phenyl or benzyl substituent and, if desired, additionally one to three further $C_1$–$C_4$-alkyl radicals, preferably diisopropylammonium, tetramethylammonium, tetrabutylammonium, trimethylbenzylammonium, furthermore phosphonium ions, preferably tri-($C_1$–$C_4$-alkyl)phosphonium, sulfonium ions, preferably tri($C_1$–$C_4$-alkyl)sulfonium, and sulfoxonium ions, preferably tri($C_1$–$C_4$-alkyl)sulfoxonium.

Anions of useful acid addition salts are mainly fluoride, chloride, bromide, hydrogen sulfate, sulfate, dihydrogen phosphate, hydrogen phosphate, phosphate, nitrate, hydrogen carbonate, carbonate, hexafluorosilicate, hexafluorophosphate, benzoate, oxalate, dodecylbenzenesulfonate, and the anions of $C_1$–$C_4$-alkanoic acids, preferably formate, acetate, propionate and butyrate.

The organic moieties mentioned for the substituents $R^1$ to $R^3$ and $R^6$ to $R^8$ or as radicals on X represent collective terms for individual enumerations of the individual group members. All carbon chains, i.e. all alkyl, haloalkyl, hydroxyalkyl, cyanoalkyl, aminoalkyl, hydroxycarbonylalkyl, aminocarbonylalkyl, alkoxy, haloalkoxy, alkylthio, haloalkylthio, alkylsulfinyl, halosulfinyl, alkylsulfonyl, haloalkylsulfonyl, alkylamino, dialkylamino, alkenyl, haloalkenyl, cyanoalkenyl, alkenyloxy, alkenylthio, alkenylsulfinyl, alkenylsulfonyl, alkynyl, haloalkynyl, cyanoalkynyl, alkynyloxy, alkynylthio, alkynylsulfinyl, alkynylsulfonyl moieties, can be straight-chain or branched. Halogenated substituents preferably have attached to them one to five identical or different halogen atoms.

The meaning of halogen is in each case fluorine, bromine, chlorine or iodine, in particular fluorine or chlorine.

Other examples of meanings are:

$C_1$–$C_4$-alkyl: methyl, ethyl, n-propyl, 1-methylethyl, n-butyl, 1-methylpropyl, 2-methylpropyl or 1,1-dimethylethyl, in particular methyl or ethyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl, in particular chloromethyl, fluoromethyl, difluoromethyl, trifluoromethyl, 2-fluoroethyl, 2-chloroethyl or 2,2,2-trifluoroethyl;

$C_1$–$C_6$-alkyl: $C_1$–$C_4$-alkyl as mentioned above and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-methyl-1-methylpropyl or 1-ethyl-2-methylpropyl, in particular methyl, ethyl, n-propyl, 1-methylethyl, n-butyl, 1,1-dimethylethyl, n-pentyl or n-hexyl;

$C_1$–$C_6$-haloalkyl: a $C_1$–$C_6$-alkyl radical as mentioned above which is partially or fully substituted by fluorine, chlorine, bromine and/or iodine, i.e., for example, one of the radicals mentioned under $C_1$–$C_4$-haloalkyl, or 5-fluoro-1-pentyl, 5-chloro-1-pentyl, 5-bromine-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl, in particular chloromethyl, fluoromethyl, difluoromethyl, trifluoromethyl, 2-fluoroethyl, 2-chloroethyl or 2,2,2-trifluoroethyl;

hydroxy-$C_1$–$C_4$-alkyl: for example hydroxymethyl, 2-hydroxyeth-1-yl, 2-hydroxyprop-1-yl, 3-hydroxyprop-1-yl, 1-hydroxyprop-2-yl, 2-hydroxybut-1-yl, 3-hydroxybut-1-yl, 4-hydroxybut-1-yl, 1-hydroxybut-2-yl, 1-hydroxybut-3-yl, 2-hydroxybut-3-yl, 1-hydroxy-2-methylprop-3-yl, 2-hydroxy-2-methylprop-3-yl, or 2-hydroxymethylprop-2-yl, in particular 2-hydroxyethyl;

cyano-$C_1$–$C_4$-alkyl: cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3- yl, 2-cyano-2-methylprop-3-yl, 3-cyano-2-methylprop-3-yl or 2-cyanomethylprop-2-yl, in particular cyanomethyl or 2-cyanoethyl;

amino-$C_1$–$C_4$-alkyl: for example aminomethyl, 2-aminoethyl, 2-aminoprop-1-yl, 3-aminoprop-1-yl, 2-aminobut-1-yl, 3-aminobut-1-yl, 4-aminobut-1-yl, 1-aminobut-2-yl, 3-aminobut-2-yl, 4-aminobut-2-yl, 1-(aminomethyl)eth-1-yl, 1-(aminomethyl)-1-(methyl)eth-1-yl or 1-(aminomethyl)prop-1-yl, in particular aminomethyl or 2-aminoethyl;

hydroxycarbonyl-$C_1$–$C_4$-alkyl: hydroxycarbonylmethyl, 1-(hydroxycarbonyl)ethyl, 2-(hydroxycarbonyl)ethyl, 1-(hydroxycarbonyl)prop-1-yl, 2-(hydroxycarbonyl)prop-1-yl, 3-(hydroxycarbonyl)prop-1-yl, 1-(hydroxycarbonyl)but-1-yl, 2-(hydroxycarbonyl)but-1-yl, 3-(hydroxycarbonyl)but-1-yl, 4-(hydroxycarbonyl)but-1-yl, 1-(hydroxycarbonyl)but-2-yl, 2-(hydroxycarbonyl(but-2-yl, 3-(hydroxycarbonyl)but-2-yl, 4-(hydroxycarbonyl)but-2-yl, 1-(hydroxycarbonylmethyl)eth-1-yl, 1-(hydroxycarbonylmethyl)-1-(methyl)eth-1-yl or 1-(hydroxycarbonylmethyl)prop-1-yl, in particular hydroxycarbonylmethyl or 2-(hydroxycarbonyl)ethyl;

aminocarbonyl-$C_1$–$C_4$-alkyl: aminocarbonylmethyl, 1-(aminocarbonyl)ethyl, 2-(aminocarbonyl)ethyl, 1-(aminocarbonyl)prop-1-yl, 2-(aminocarbonyl)prop-1-yl, 3-(aminocarbonyl)prop-1-yl, 1-(aminocarbonyl)but-1-yl, 2-(aminocarbonyl)but-1-yl, 3-(aminocarbonyl)but-1-yl, 4-(aminocarbonyl)but-1-yl, 1-(aminocarbonyl)but-2-yl, 2-(aminocarbonyl)but-2-yl, 3-(aminocarbonyl)but-2-yl, 4-(aminocarbonyl)but-2-yl, 1-(aminocarbonyl)eth-1-yl, 1-(aminocarbonylmethyl)-1-(methyl)eth-1-yl or 1-(aminocarbonylmethyl)prop-1-yl, in particular aminocarbonylmethyl or 2-(aminocarbonyl)ethyl;

phenyl-$C_1$–$C_4$-alkyl: benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(phenylmethyl)eth-1-yl, 1-(phenylmethyl)-1-(methyl)eth-1-yl, or 1-(phenylmethyl)prop-1-yl, in particular benzyl or 2-phenylethyl;

heterocyclyl-$C_1$–$C_4$-alkyl: heterocyclylmethyl, 1-heterocyclylethyl, 2-heterocyclyethyl, 1-heterocyclylprop-1-yl, 2-heterocyclylprop-1-yl, 3-heterocyclylprop-1-yl, 1-heterocyclylbut-1-yl, 2-heterocyclylbut-1-yl, 3-heterocyclylbut-1-yl, 4-heterocyclylbut-1-yl, 1-heterocyclylbut-2-yl, 2-heterocyclylbut-2-yl, 3-heterocyclylbut-2-yl, 4-heterocyclybut-2-yl, 1-(heterocyclylmethyl)eth-1-yl, 1-(heterocyclylmethyl)- 1-(methyl)eth-1-yl or 1-(heterocyclylmethyl)prop-1-yl, in particular heterocyclylmethyl, 2-heterocyclylethyl or 3-heterocyclylpropyl; 3-oxetanylmethyl, 2-(1,3-oxazolin-2-on-3yl)ethyl and 3-(2-pyridyl)propyl are especially preferred;

($C_1$–$C_4$-alkyl)carbonyl: $CO$—$CH_3$, $CO$—$C_2H_5$, n-propylcarbonyl, 1-methylethylcarbonyl, n-butylcarbonyl, $CO$—$CH(CH_3)_2$, 2-methylpropylcarbonyl or $CO$—$C(CH_3)_3$, in particular $CO$—$CH_3$;

($C_1$–$C_4$-haloalkyl)carbonyl: a ($C_1$–$C_4$-alkyl)carbonyl radical as mentioned above which is partially or fully substituted by fluorine, chlorine, bromine and/or iodine, i.e., for example, chloroacetyl, dichloroacetyl, trichloroacetyl, fluoroacetyl, difluoroacetyl, trifluoroacetyl, chlorofluoroacetyl, dichlorofluoroacetyl, chlorodifluoroacetyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, $CO$—$C_2F_5$, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, 2,2,3,3,3-pentafluoropropylcarbonyl, heptafluoropropylcarbonyl, 1-(fluoromethyl)-2-fluoroethylcarbonyl, 1-(chloromethyl)-2-chloroethylcarbonyl, 1-(bromomethyl)-2-bromoethylcarbonyl, 4-fluorobutylcarbonyl, 4-chlorobutylcarbonyl, 4-bromobutylcarbonyl or nonafluorobutylcarbonyl, in particular trifluoroacetyl;

($C_1$–$C_4$)carbonyloxy: acetyloxy, ethylcarbonyloxy, n-propylcarbonyloxy, 1-methylethylcarbonyloxy, n-butylcarbonyloxy, 1-methylpropylcarbonyloxy, 2-methylpropylcarbonloxy or 1,1-dimethylethylcarbonyloxy, in particular acetyloxy;

($C_1$–$C_4$-haloalkyl)carbonyloxy: a ($C_1$–$C_4$-alkyl)carbonyloxy radical as mentioned above which is partially or fully substituted by fluorine, chlorine, bromine and/or iodine, i.e., for example, chloroacetyloxy, dichloroacetyloxy, trichloroacetyloxy, fluoroacetyloxy, difluoroacetyloxy, trifluoroacetyloxy, chlorofluoroacetyloxy, dichlorofluoroacetyloxy, chlorodifluoroacetyloxy, 2-fluoroethylcarbonyloxy, 2-chloroethylcarbonyloxy, 2-bromoethylcarbonyloxy, 2-iodoethylcarbonyloxy, 2,2-difluoroethylcarbonyloxy, 2,2,2-trifluoroethylcarbonyloxy, 2-chloro-2-fluoroethylcarbonyloxy, 2-chloro-2,2-difluoroethylcarbonyloxy, 2,2-dichloro-2-fluoroethylcarbonyloxy, 2,2,2-trichloroethylcarbonyloxy, pentafluoroethylcarbonyloxy, 2-fluoropropylcarbonyloxy, 3-fluoropropylcarbonyloxy, 2,2-difluoropropylcarbonyloxy, 2,3-difluoropropylcarbonyloxy, 2-chloropropylcarbonyloxy, 3-chloropropylcarbonyloxy, 2,3-dichloropropylcarbonyloxy, 2-bromopropylcarbonyloxy, 3-bromopropylcarbonyloxy, 3,3,3-trifluoropropylcarbonyloxy, 3,3,3-trichloropropylcarbonyloxy, 2,2,3,3,3-pentafluoropropylcarbonyloxy, heptafluoropropylcarbonyloxy, 1-(fluoromethyl)-2-fluoroethylcarbonyloxy, 1-(chloromethyl)-2-chloroethylcarbonyloxy, 1-(bromomethyl)-2-bromoethylcarbonyloxy, 4-fluorobutylcarbonyloxy, 4-chlorobutylcarbonyloxy, 4-bromobutyl or nonafluorobutyl, in particular trifluoroacetoxy;

$C_1$–$C_4$-alkoxy: methoxy, ethoxy, n-propoxy, 1-methylethoxy, n-butoxy, 1-methylpropoxy, 2-methylpropoxy or 1,1-dimethylethoxy, in particular methoxy or ethoxy;

$C_1$–$C_4$-haloalkoxy: a $C_1$–$C_4$-alkoxy radical as mentioned above which is partially or fully substituted by fluorine, chlorine, bromine and/or iodine, i.e., for example, chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy, in particular 2-chloroethoxy or 2,2,2-trifluoroethoxy;

($C_1$–$C_4$-alkoxy)carbonyl: methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl or 1,1-dimethylethoxycarbonyl, in particular methoxycarbonyl or ethoxycarbonyl;

$C_1$–$C_6$-alkylthio: methylthio, ethylthio, n-propylthio, 1-methylethylthio, n-butylthio, 1-methylpropylthio, 2-methylpropylthio or 1,1-dimethylethylthio, in particular methylthio or ethylthio;

$C_1$–$C_4$-alkylamino: methylamino, ethylamino, n-propylamino, 1-methylethylamino, n-butylamino, 1-methylpropylamino, 2-methylpropylamino or 1,1-dimethylethylamino, in particular methylamino or ethylamino;

di($C_1$–$C_4$-alkyl)amino: N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethyl-ethyl)-N-(1-methylpropyl)amino or N-(1,1-dimethyl-ethyl)-N-(2-methylpropyl)amino, in particular N($CH_3$)$_2$ or N($C_2H_5$)$_2$;

$C_1$–$C_4$-alkoxy-$C_1$–$C_4$-alkyl: $C_1$–$C_4$-alkyl which is substituted by $C_1$–$C_4$-alkoxy as mentioned above, i.e., for example, methoxymethyl, ethoxymethyl, n-propoxymethyl, (1-methylethoxy)methyl, n-butoxymethyl, (1-methylpropoxy)methyl, (2-methylpropoxy)methyl, (1,1-dimethylethoxy)methyl, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, in particular methoxymethyl or 2-methoxyethyl;

($C_1$–$C_4$-alkoxy)carbonyl-$C_1$–$C_4$-alkyl: $C_1$–$C_4$-alkyl which is substituted by ($C_1$–$C_4$-alkoxy)carbonyl as mentioned above, i.e., for example, methoxycarbonylmethyl, ethoxycarbonylmethyl, 1-(methoxycarbonyl)ethyl or 2-(methoxycarbonyl)ethyl;

$C_1$–$C_4$-alkylthio-$C_1$–$C_4$-alkyl: $C_1$–$C_4$-alkyl which is substituted by $C_1$–$C_4$-alkylthio as mentioned above, i.e., for example, methylthiomethyl, ethylthiomethyl, n-propylthiomethyl, (1-methylethylthio)methyl, n-butylthiomethyl, (1-methylpropylthio)methyl, (2-methylpropylthio)methyl, (1,1-dimethylethylthio)methyl, 2-methylthioethyl, 2-ethylthioethyl, 2-(n-propylthio)ethyl, 2-(1-methylethylthio)ethyl, 2-(n-butylthio)ethyl, 2-(1-methylpropylthio)ethyl, 2-(2-methylpropylthio)ethyl, 2-(1,1-dimethylethylthio)ethyl, 2-(methylthio)propyl, 3-(methylthio)propyl, 2-(ethylthio)propyl, 3-(ethylthio)propyl, 3-(propylthio)propyl, 3-(butylthio)propyl, 4-(methylthio)butyl, 4-(ethylthio)butyl, 4-(n-propylthio)butyl, or 4-(n-butylthio)butyl, in particular 2-(methylthio)ethyl;

($C_1$–$C_4$-alkylthio)carbonyl-$C_1$–$C_4$-alkyl: $C_1$–$C_4$-alkyl which is substituted by ($C_1$–$C_4$-alkylthio)carbonyl such as (methylthio)carbonyl, (ethylthio)carbonyl, (n-propylthio)carbonyl, (1-methylethylthio)carbonyl, (n-butylthio)carbonyl, (1-methylpropylthio)carbonyl, (2-methylpropylthio)carbonyl and (1,1-dimethylethylthio)carbonyl, preferably (methylthio)carbonyl or (ethylthio)carbonyl, i.e., for example, (methylthio)carbonylmethyl, (ethylthio)carbonylmethyl, 1-[(methylthio)carbonyl]ethyl or 2-[(methylthio)carbonyl]ethyl;

$C_1$–$C_4$-haloalkylthio-$C_1$–$C_4$-alkyl: $C_1$–$C_4$-alkyl as mentioned above which as attached to it a $C_1$–$C_4$-alkylthio group which is partially or fully substituted by fluorine, chlorine and/or bromine, e.g. difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trifluoroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio or 4-bromobutylthio, i.e., for example, difluoromethylthiomethyl;

$C_1$–$C_4$-alkylamino-$C_1$–$C_4$-alkyl: $C_1$–$C_4$-alkyl which is substituted by $C_1$–$C_4$-alkylamino as mentioned above, i.e., for example, methylaminomethyl, ethylaminomethyl, n-propylaminomethyl, (1-methylethylamino)methyl, n-butylaminomethyl, (1-methylpropylamino)methyl, (2-methylpropylamino)methyl, (1,1-dimethylethylamino)methyl, 2-methylaminoethyl, 2-ethylaminoethyl, 2-(n-propylamino)ethyl, 2-(1-methylethylamino)ethyl, 2-(n-butylamino)ethyl, 2-(1-methylpropylamino)ethyl, 2-(2-methylpropylamino)ethyl, 2-(1,1-dimethylethylamino)

ethyl, 2-(methylamino)propyl, 3-(methylamino)propyl, 2-(ethylamino)propyl, 3-(ethylamino)propyl, 3-(propylamino)propyl, 3-(butylamino)propyl, 4-(methylamino)butyl, 4-(ethylamino)butyl, 4-(n-propylamino)butyl or 4-(n-butylamino)butyl, in particular 2-(methylamino)ethyl;

$C_1$–$C_4$-alkylaminocarbonyl-$C_1$–$C_4$-alkyl: $C_1$–$C_4$-alkyl which is substituted by $C_1$–$C_4$-alkylaminocarbonyl such as methylaminocarbonyl, ethylaminocarbonyl, n-propylaminocarbonyl, 1-methylethylaminocarbonyl, n-butylaminocarbonyl, 1-methylpropylaminocarbonyl, 2-methylpropylaminocarbonyl or 1,1-dimethylethylaminocarbonyl, preferably methylaminocarbonyl or ethylaminocarbonyl, i.e., for example, (methylaminocarbonyl)methyl, (ethylaminocarbonyl) methyl, 1-(methylaminocarbonyl)ethyl or 2-(methylaminocarbonyl)ethyl;

di($C_1$–$C_4$-alkyl)amino-$C_1$–$C_4$-alkyl: $C_1$–$C_4$-alkyl which is substituted by di($C_1$–$C_4$-alkyl)amino as mentioned above, i.e., for example, dimethylaminomethyl or diethylaminomethyl;

di($C_1$–$C_4$-alkyl)aminocarbonyl-$C_1$–$C_4$-alkyl: $C_1$–$C_4$-alkyl which is substituted by di($C_1$–$C_4$-alkyl)aminocarbonyl such as N,N-dimethylaminocarbonyl, N,N-diethylaminocarbonyl, N,N-dipropylaminocarbonyl, N,N-di(1-methylethyl)aminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl) aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl) aminocarbonyl, N-methyl-N-(2-methylpropyl) aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl) aminocarbonyl, N-ethyl-N-(2-methylpropyl) aminocarbonyl, N-ethyl-N-(1,1-dimethylethyl) aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propyl-aminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl) aminocarbonyl, N-butyl-N-(2-methylpropyl) aminocarbonyl, N-butyl-N-(1,1-dimethylethyl) aminocarbonyl, N-(1-methylpropyl)-N-(2-methylpropyl) aminocarbonyl, N-(1,1-dimethylethyl)-N-(1-methylpropyl) aminocarbonyl or N-(1,1-dimethylethyl)-N-(2-methylpropyl)aminocarbonyl, preferably N,N-dimethylaminocarbonyl or N,N-diethylaminocarbonyl, i.e., for example, dimethylaminocarbonylmethyl, diethylaminocarbonylmethyl, 1-(dimethylaminocarbonyl) ethyl or 2-(dimethylaminocarbonyl)ethyl;

$C_1$–$C_4$-alkylsulfinyl-$C_1$–$C_4$-alkyl: $C_1$–$C_4$-alkyl which is substituted by methylsulfinyl, ethylsulfinyl, n-propylsulfinyl, 1-methylethylsulfinyl, n-butylsulfinyl, 1-methylpropylsulfinyl, 2-methylpropylsulfinyl or 1,1-dimethylethylsulfinyl, preferably methylsulfinyl, i.e, for example, methylsulfinylmethyl or 2-methylsulfinylethyl;

$C_1$–$C_4$-haloalkylsulfinyl-$C_1$–$C_4$-alkyl: $C_1$–$C_4$-alkyl as mentioned above which as attached to it a $C_1$–$C_4$-alkylsulfinyl group which is partially or fully substituted by fluorine, chlorine, and/or bromine, e.g. difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl or 4-bromobutylsulfinyl, i.e., for example, difluoromethylsulfinylmethyl;

$C_1$–$C_4$-alkylsulfonyl: methylsulfonyl, ethylsulfonyl, n-propylsulfonyl, 1-methylethylsulfonyl, n-butylsulfonyl, 1-methylpropylsulfonyl, 2-methylpropylsulfonyl or 1,1-dimethylethylsulfonyl, in particular methylsulfonyl or ethylsulfonyl;

$C_1$–$C_4$-alkylsulfonyl-$C_1$–$C_4$-alkyl: $C_1$–$C_4$-alkyl which is substituted by $C_1$–$C_4$-alkylsulfonyl as mentioned above, preferably methylsulfonyl, i.e., for example, methylsulfonylmethyl or 2-methylsulfonylethyl;

$C_1$–$C_4$-haloalkylsulfonyl-$C_1$–$C_4$-alkyl: $C_1$–$C_4$-alkyl as mentioned above which has attached to it a $C_1$–$C_4$-alkylsulfonyl group which is partially or fully substituted by fluorine, chlorine and/or bromine, e.g. difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2,2,2-trichloroethylsulfonyl, 2-chloro-2-fluoroethylsulfonyl, 2-chloro-2,2-difluoroethylsulfonyl, 2,2-dichloro-2-fluoroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonly, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, or 4-bromobutylsulfonyl, i.e., for example, 2-chloroethylsulfonyl;

$C_3$–$C_6$-alkenyl: for example prop-2-en-1-yl, n-buten-4-yl, 1-methylprop-2-en-1-yl, 2-methylprop-2-en-1-yl, 2-buten-1-yl, n-penten-3-yl, n-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, n-hex-3-en-1-yl, n-hex-4-en-1-yl, n-hex-5-en-1-yl, 1-methylpent-3-en-1-yl, 2-methylpent-3-en-1-yl, 3-methylpent-3-en-1-yl, 4-methyl-pent-3-en-1-yl , 1-methylpent-4-en-1-yl, 2-methyl-pent-4-en-1-yl, 3-methylpent-4-en-1-yl, 4-methyl-pent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3- dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl, in particular prop-2-en-1-yl or n-buten-4-yl;

$C_3$–$C_6$-haloalkenyl: $C_3$–$C_6$-alkenyl as mentioned above which is partially or fully substituted by fluorine, chlorine and/or bromine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl, in particular 2-chloroallyl or 3,3-dichloroallyl;

cyano-$C_3$–$C_6$-alkenyl: for example 3-cyanoallyl, 4-cyanobut-2-enyl, 4-cyanobut-3-enyl or 5-cyanopent-4-enyl, preferably 3-cyanoallyl or 4-cyanobut-2-enyl, in particular 3-cyanoallyl;

$C_3$–$C_4$-alkenyloxy-$C_1$–$C_4$-alkyl: $C_1$–$C_4$-alkyl which is substituted by $C_3$–$C_4$-alkenyloxy such as prop-2-enyloxy, n-but-2-enyloxy, n-but-3-enyloxy, 1-methylprop-2-enyloxy or 2-methylprop-2-enyloxy, preferably allyloxy, 2-methylprop-2-en-1-yloxy, but-1-en-3-yloxy, but-1-en-4-yloxy or but-2-en-1-yloxy, i.e., for example, allyloxymethyl, 2-allyloxyethyl or but-1-en-4-yloxylmethyl;

$C_3$–$C_4$-alkenylthio-$C_1$–$C_4$-alkyl which is substituted by $C_3$–$C_4$-alkenylthio such as prop-2-enylthio, n-but-2-enylthio, n-but-3-enylthio, 1-methylprop-2-enylthio or 2-methylprop-2-enylthio, preferably allylthio, 2-methylprop-2-en-1-ylthio, but-1-en-3-ylthio, but-1-en-4-ylthio or but-2-en-1-ylthio, i.e., for example, allylthiomethyl, 2-allythioethyl or but-1-en-4-ylthiomethyl;

$C_3$–$C_4$-alkenylsulfinyl-$C_1$–$C_4$-alkyl: $C_1$–$C_4$-alkyl which is substituted by $C_3$–$C_4$-alkenylsulfinyl such as prop-2-enylsulfinyl, n-but-2-enylsulfinyl, n-but-3-enylsulfinyl, 1-methylprop-2-enylsulfinyl or 2-methylprop-2-enylsulfinyl, preferably allylsulfinyl, 2-methylprop-2-en-1-ylsulfinyl, but-1-en-3-ylsulfinyl, but-1-en-4-ylsulfinyl or but-2-en-1-ylsulfinyl, i.e., for example, allylsulfinylmethyl, 2-allylsulfinylethyl or but-1-en-4-ylsulfinylmethyl;

$C_3$–$C_4$-alkenylsulfonyl-$C_1$–$C_4$-alkyl: $C_1$–$C_4$-alkyl which is substituted by $C_3$–$C_4$-alkenylsulfonyl such as prop-2-enylsulfonyl, n-but-2-enylsulfonyl, n-but-3-enylsulfonyl, 1-methylprop-2-enylsulfonyl or 2-methylprop-2-enylsulfonyl, preferably allylsulfonyl, 2-methylprop-2-en-1-ylsulfonyl, but-1-en-3-ylsulfonyl, but-1-en-4-ylsulfonyl or but-2-en-1-ylsulfonyl, i.e., for example, allylsulfonylmethyl, 2-allylsulfonylethyl or but-1-en-4-ylsulfonylmethyl;

$C_3$–$C_6$-alkynyl: for example propargyl, n-but-1-yn-3-yl, n-but-1-yn-4-yl, n-but-2-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-3-yl, 3-methyl-but-1-yn-4-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl, in particular propargyl;

$C_3$–$C_6$-haloalkynyl: $C_3$–$C_6$-alkynyl as mentioned above which is partially or fully substituted by fluorine, chlorine and/or bromine, i.e., for example, 1,1-difluoroprop-2-yn-1-yl, 4-fluorobut-2-yn-1-yl, 4-chlorobut-2-yn-1-yl, 1,1-difluorobut-2-yn-1-yl, 5-fluoropent-3-yn-1-yl or 6-fluorohex-4-yn-1-yl;

cyano-$C_3$–$C_6$-alkynyl: for example 3-cyanopropargyl;

$C_3$–$C_4$-alkynyloxy-$C_1$–$C_4$-alkyl: $C_1$–$C_4$-alkyl which is substituted by $C_3$–$C_4$-alkynyloxy such as prop-2-ynyloxy, n-but-2-ynyloxy, n-but-3-ynyloxy or 1-methylprop-2-ynyloxy, preferably propargyloxy, but-1-yn-3-yloxy, but-1-yn-4-yloxy or but-2-yn-1-yloxy, i.e., for example, propargyloxymethyl or 2-propargyloxyethyl;

$C_3$–$C_4$-alkynylthio-$C_1$–$C_4$-alkyl: $C_1$–$C_4$-alkyl which is substituted by $C_3$–$C_4$-alkynylthio such as prop-2-ynylthio, n-but-2-ynylthio, n-but-3-ynylthio or 1-methylprop-2-ynylthio, preferably propargylthio, but-1-yn-3-ylthio, but-1-yn-4-ylthio or but-2-yn-1-ylthio, i.e., for example, propargylthiomethyl or 2-propargylthioethyl;

$C_3$–$C_4$-alkynylsulfinyl-$C_1$–$C_4$-alkyl which is substituted by $C_3$–$C_4$-alkynylsulfinyl such as prop-2-ynylsulfinyl, n-but-2-ynylsulfinyl, n-but-3-ynylsulfinyl and 1-methylprop-2-ynylsulfinyl, preferably propargylsulfinyl, but-1-yn-3-ylsulfinyl, but-1-yn-4-ylsulfinyl or but-2-yn-1-ylsulfinyl, i.e., for example, propargylsulfinylmethyl or 2-propargylsulfinylethyl;

$C_3$–$C_4$-alkynylsulfonyl-$C_1$–$C_4$-alkyl: $C_1$–$C_4$-alkyl which is substituted by $C_3$–$C_4$-alkynylsulfonyl such as prop-2-ynylsulfonyl, n-but-2-ynylsulfonyl, n-but-3-ynylsulfonyl and 1-methylprop-2-ynylsulfonyl, preferably propargylsulfonyl, but-1-yn-3-ylsulfonyl, but-1-yn-4-ylsulfonyl or but-2-yn-1-ylsulfonyl, i.e., for example, propargylsulfonylmethyl or 2-propargylsulfonylethyl;

$C_3$–$C_8$-cycloalkyl: cyclopropyl, cyclobutyl, cyclopentyl, cyclohexyl, cycloheptyl or cyclooctyl, in particular cyclopentyl or cyclohexy;

$C_3$–$C_8$-cycloalkyl-$C_1$–$C_4$-alkyl: cyclopropylmethyl, cyclobutylmethyl, cyclopentylmethyl, cyclohexylmethyl, cycloheptylmethyl, cyclooctylmethyl, 1-(cyclopropyl)ethyl, 1-(cyclobutyl)ethyl, 1-(cyclopentyl)ethyl, 1-(cyclohexyl)ethyl, 1-(cycloheptylethyl, 1-(cyclooctyl)ethyl, 2-cyclopropyl)ethyl, 2-(cyclobutyl)ethyl, 2-(cyclopentyl)ethyl, 2-(cyclohexyl)ethyl, 2-(cycloheptyl)ethyl, 2-(cyclooctyl)ethyl, 3-(cyclopropy)propyl, 3-(cyclobutyl)propyl, 3-(cyclopentyl)propyl, 3-(cyclohexyl)propyl, 3-(cycloheptyl)propyl, 3-(cyclooctyl)propyl, 4-(cyclopropyl)butyl, 4-(cyclobutyl)butyl, 4-(cyclobutyl)butyl, 4-(cyclopentyl)butyl, 4-(cyclohexyl)-butyl, 4-(cycloheptyl)butyl or 4-(cyclooctyl)butyl, in particular cyclopentylmethyl or cyclohexylmethyl;

$C_3$–$C_8$-cycloalkoxy-$C_1$–$C_4$-alkyl: cyclopropyloxymethyl, cyclobutyloxymethyl, cyclopentyloxymethyl, cyclohexyloymethyl, cycloheptyloxymethyl, cyclooctyloxymethyl, 1-(cyclopropyloxy)ethyl, 1-(cyclobutyloxy)ethyl, 1-(cyclopentyloxy)ethyl, 1-(cyclohexyloxy)ethyl, 1-(cycloheptyloxy)ethyl, 1-(cyclooctyloxy)ethyl, 2-(cyclopropyloxy)ethyl, 2-(cyclobutyloxy)ethyl, 2-(cyclopentyloxy)ethyl, 2-(cyclohexyloxy)ethyl, 2-(cycloheptyloxy)ethyl, 2-(cyclooctyloxy)ethyl, 3-(cyclopropyloxy)propyl, 3-(cyclobutyloxy)propyl, 3-(cyclopentyloxy)propyl, 3-(cyclohexyloxy)propyl, 3-(cycloheptyloxy)propyl, 3-(cyclooctyploxy)propyl, 4-(cyclopropyloxy)butyl, 4-(cyclobutyloxy)butyl, 4-(cyclopentyloxy)butyl, 4-(cyclohexyloxy)butyl, 4-(cycloheptyloxy)butyl 4-(cycloheptyloxy)butyl or 4-(cyclooctyloxy)butyl, in particular cyclopentyloxymethyl, cyclohexyloxymethyl or 2-(cyclopentyloxy)ethyl.

3- to 7-membered heterocyclyl is to be understood as meaning both saturated, partially or fully unsaturated and aromatic heterocycles having one to three hetero atoms selected from a group consisting of one to three nitrogen atoms,
one or two oxygen and
one or two sulfur atoms.

Examples of saturated heterocycles which can contain a carbonyl or thiocarbonyl ring member are:

oxiranyl, thiiranyl, aziridin-1-yl, aziridin-2-yl, diaziridin-1-yl, diaziridin-3-yl, oxetan-2-yl, oxetan-3yl, thietan-2-yl, thietan-3-yl, azetidin-1-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-2-yl, 1,3-dithiepan-2-yl, 1,3-dithiepan-2-yl, 1,4-dioxepan-2-yl, 1,4-dioxepan-7-yl, hexahydroazepin-1-yl, hexahydroazepin-2-yl, hexahydroazepin-3-yl, hexahydroazepin-4-yl, hexahydro-1,3-diazepin-1-yl, hexahydro-1,3-diazepin- 2-yl, hexahydro-1,3-diazepin-4-yl, hexahydro-1,4-diazepin-1-yl and hexahydro-1,4-diazepin-2-yl;

Examples of unsaturated heterocycles which can contain a carbonyl or thiocarbonyl ring member are: dihydrofuran-2-yl, 1,2-oxazolin-3-yl, 1,2-oxazolin-5-yl, 1,3-oxazolin-2-yl;

Preferred amongst the heteroaromatics are those having 5 or 6 members, i.e., for example, furyl such as 2-furyl and 3-furyl, thienyl such as 2-thienyl and 3-thienyl, pyrrolyl such as 2-pyrrolyl and 3-pyrrolyl, isoxazolyl such as 3-isoxazolyl, 4-isoxazolyl and 5-isoxazolyl, isothiazolyl such as 3-isothiazolyl, 4-isothiazolyl and 5-isothiazolyl, pyrazolyl such as 3-pyrazolyl, 4-pyrazolyl and 5-pyrazolyl, oxazolyl such as 2-oxazolyl, 4-oxazolyl and 5-oxazolyl, thiazolyl such as 2-thiazolyl, 4-thiazolyl and 5-thiazolyl, imidazolyl such as 2-imidazolyl and 4-imidazolyl, oxadiazolyl such as 1,2,4-oxadiazol-3-yl, 1,2,4-oxadiazol-5-yl and 1,3,4-oxadiazol-2-yl, thiadiazolyl such as 1,2,4-thiadiazol-3-yl, 1,2,4-thiadiazol-5-yl and 1,3,4-thiadiazol-2-yl, triazolyl such as 1,2,4-triazol-1-yl, 1,2,4-triazol-3-yl and 1,2,4-triazol-4-yl, pyridinyl such as 2-pyridinyl, 3-pyridinyl and 4-pyridinyl, pyridazinyl such as 3-pyridazinyl and 4-pyridazinyl, pyrimidinyl such as 2-pyrimidinyl, 4-pyrimidinyl and 5-pyrimidinyl, furthermore 2-pyrazinyl, 1,3,5-triazin-2-yl and 1,2,4-triazin-3-yl, in particular pyridyl, pyrimidyl, furanyl and thienyl.

All phenyl and heterocyclic rings are preferably unsubstituted or have attached to them a cyano, nitro, halogen, $C_1$–$C_4$-alkyl, $C_1$–$C_4$-haloalkyl, $C_1$–$C_4$-alkoxy, $C_1$–$C_4$-haloalkoxy, ($C_1$–$C_4$-alkyl)carbonyl, ($C_1$–$C_4$-alkoxy)carbonyl or ($C_1$–$C_4$-alkyl)carbonyloxy substituent.

With a view to the use of the substituted 2-phenylpyridines I as herbicides or for the desiccation/defoliation of plants, preferred compounds I are those where the substituents have the following meanings, in each case alone or in combination:

X is 1,2-ethyndiyl, ethylene, 1,2-ethyanediyl, methyleneoxymethylene, ethene-1,2-diyl, or oxymethylene which is bonded to the phenyl ring via the hetero atom, it being possible for the last-mentioned 5 bridges to have attached, to the carbon atom adjacent to the phosphorus, one of the following substituents: cyano, halogen, $C_1$–$C_4$-alkyl or ($C_1$–$C_4$-alkoxy)carbonyl; in particular —CH$_2$—, —CH$_2$CH$_2$—, —CH$_2$—CH(halogen)—, —CH$_2$—CH(CN)—, —CH$_2$—CH(CH$_3$)—, —CH$_2$—CH(COOCH$_3$)—, —CH$_2$—O—CH$_2$—, —CH=CH—, —CH=C(halogen)—, —CH=C(CN)—, —CH=C(CH$_3$)—, —CH=C(COOCH$_3$)—, —CH$_2$—CH(COOCH$_3$)— or —OCH$_2$—; especially preferably —CH$_2$—CH(halogen)— or —CH=C(halogen)—;

Y is oxygen; $Z^1$ is oxygen; $Z^2$ is oxygen;

$R^1$, $R^2$, $R^7$ and $R^8$, independently of one another, are hydrogen, $C_1$–$C_6$-alkyl, $C_1$–$C_6$-haloalkyl, cyano-$C_1$–$C_4$-alkyl, $C_1$–$C_4$-alkoxy-$C_1$–$C_4$- alkyl, di($C_1$–$C_4$-alkyl)amino-$C_1$–$C_4$-alkyl, $C_1$–$C_4$-alkylthio-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, $C_3$–$C_6$-alkenyl, $C_3$–$C_6$-haloalkenyl, $C_3$–$C_6$-alkynyl, hydroxycarbonyl-$C_1$–$C_4$-alkyl, ($C_1$–$C_4$-alkoxy)carbonyl-$C_1$–$C_4$-alkyl, aminocarbonyl-$C_1$–$C_4$-alkyl, ($C_1$–$C_4$-alkyl)aminocarbonyl-$C_1$–$C_4$-alkyl, di($C_1$–$C_4$-alkyl)aminocarbonyl-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl or 3- to 7-membered heterocyclyl or heterocyclyl-$C_1$–$C_4$-alkyl, it being possible for all heterocycles, if desired, to contain a carbonyl or thiocarbonyl ring member and it being possible for all cycloalkyl, phenyl and heterocyclyl rings to be unsubstituted or to have attached to them one to four substituents, in each case selected from the group consisting of halogen, nitro, amino, hydroxyl, carboxyl, $C_1$–$C_4$-alkyl, $C_1$–$C_4$-haloalkyl, $C_1$–$C_4$-alkoxy, $C_1$–$C_4$-alkylsulfonyl, ($C_1$–$C_4$-alkyl)carbonyl, ($C_1$–$C_4$-alkoxy)carbonyl and di($C_1$–$C_4$-alkyl)amino, or $R^1$ and $R^2$ or $R^1$ and $R^7$ and/or $R^2$ and $R^8$ in each case together form a 1,2-ethanediyl, 1,3-propylene, tetramethylene, pentamethylene or ethyleneoxyethylene chain which, if desired, can be substituted by one to four $C_1$–$C_4$-alkyl groups and/or one or two ($C_1$–$C_4$-alkoxy)carbonyl groups;

in particular hydrogen, $C_1$–$C_6$-alkyl, $C_1$–$C_6$-haloalkyl, $C_3$–$C_6$-alkenyl, $C_3$–$C_6$-haloalkenyl, $C_3$–$C_6$-alkynyl, ($C_1$–$C_4$-alkoxy)carbonyl-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl, 3- to 7-membered heterocyclyl or heterocyclyl-$C_1$–$C_4$-alkyl, or $R^1$ and $R^2$ and/or $R^1$ and $R^7$ and/or $R^2$ and $R^8$ in each case together form a 1,2-ethanediyl- or 1,3-propylene chain; especially preferably hydrogen, $C_1$–$C_6$-alkyl, $C_3$–$C_6$-alkenyl, $C_3$–$C_6$-alkynyl, $C_3$–$C_8$-cycloalkyl, phenyl or phenyl-$C_1$–$C_4$-alkyl, or $R^1$ and $R^2$ together form a 1,3-propylene chain;

$R^3$ is cyano, halogen or trifluoromethyl, in particular cyano or chlorine, especially preferably chlorine;

$R^4$ is hydrogen, fluorine or chlorine, in particular hydrogen or fluorine;

$R^5$ is chlorine;

$R^6$ is chlorine or trifluoromethyl, in particular trifluoromethyl;

n is zero.

Very especially preferred are the compound Iaα (= I where X=methylene; $R^3$, $R^5$=chlorine; $R^4$=hydrogen; $R^6$=trifluoromethyl; n=0) which are listed in Table 1 below:

TABLE 1

Iaα

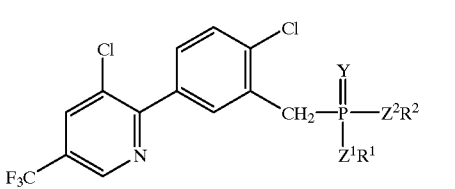

| No. | —P(=Y)($Z^1R^1$)($Z^2R^2$) |
|---|---|
| Iaα. 1 | —P(=O)(OH)$_2$ |
| Iaα. 2 | —P(=O)(OCH$_3$)$_2$ |
| Iaα. 3 | —P(=O)(OC$_2$H$_5$)$_2$ |
| Iaα. 4 | —P(=O)[O—(n-C$_3$H$_7$)]$_2$ |
| Iaα. 5 | —P(=O)[OCH(CH$_3$)$_2$]$_2$ |
| Iaα. 6 | —P(=O)[O—(n-C$_4$H$_9$)]$_2$ |
| Iaα. 7 | —P(=O)[OCH$_2$—CH(CH$_3$)$_2$]$_2$ |
| Iaα. 8 | —P(=O)[OCH(CH$_3$)—C$_2$H$_5$]$_2$ |
| Iaα. 9 | —P(=O)(OCH$_2$—CF$_3$)$_2$ |
| Iaα. 10 | —P(=O)(OCH$_2$—CH$_2$—OH)$_2$ |
| Iaα. 11 | —P(=O)(OCH$_2$—CH$_2$—CN)$_2$ |
| Iaα. 12 | —P(=O)(OCH$_2$—CH$_2$—OCH$_3$)$_2$ |
| Iaα. 13 | —P(=O)(OCH$_2$—CH$_2$—OC$_2$H$_5$)$_2$ |
| Iaα. 14 | —P(=O)(OCH$_2$—CH$_2$—OCF$_3$)$_2$ |
| Iaα. 15 | —P(=O)(OCH$_2$—CH$_2$—OCH$_2$—CH=CH$_2$)$_2$ |
| Iaα. 16 | —P(=O)(OCH$_2$—CH$_2$—OCH$_2$—C≡CH)$_2$ |
| Iaα. 17 | —P(=O)(OCH$_2$—CH$_2$—O-cyclopentyl)$_2$ |
| Iaα. 18 | —P(=O)(OCH$_2$—CH$_2$—NH$_2$)$_2$ |
| Iaα. 19 | —P(=O)(OCH$_2$—CH$_2$—NH—CH$_3$)$_2$ |
| Iaα. 20 | —P(=O)[OCH$_2$—CH$_2$—N(CH$_3$)$_2$]$_2$ |
| Iaα. 21 | —P(=O)(OCH$_2$—CH$_2$—SCH$_3$)$_2$ |
| Iaα. 22 | —P(=O)(OCH$_2$—CH$_2$—SC$_2$H$_5$)$_2$ |
| Iaα. 23 | —P(=O)(OCH$_2$—CH$_2$—SCF$_3$)$_2$ |
| Iaα. 24 | —P(=O)(OCH$_2$—CH$_2$—SCH$_2$—CH=CH$_2$)$_2$ |
| Iaα. 25 | —P(=O)(OCH$_2$—CH$_2$—SCH$_2$—C≡CH)$_2$ |
| Iaα. 26 | —P(=O)(OCH$_2$—CH$_2$—SCH$_2$—C≡CH)$_2$ |
| Iaα. 27 | —P(=O)(OCH$_2$—CH$_2$—SO—C$_2$H$_5$)$_2$ |
| Iaα. 28 | —P(=O)(OCH$_2$—SO$_2$—CH$_3$)$_2$ |
| Iaα. 29 | —P(=O)(OCH$_2$—SO$_2$—C$_2$H$_5$)$_2$ |
| Iaα. 30 | —P(=O)(OCH$_2$—CH$_2$—SO$_2$—CH$_3$)$_2$ |
| Iaα. 31 | —P(=O)(OCH$_2$—CH$_2$—SO$_2$—C$_2$H$_5$)$_2$ |
| Iaα. 32 | —P(=O)(OCH$_2$—CH=CH$_2$)$_2$ |
| Iaα. 33 | —P(=O)(OCH$_2$—CH=CH—CH$_3$)$_2$ |
| Iaα. 34 | —P(=O)(OCH$_2$—CH$_2$—CH=CH$_2$)$_2$ |
| Iaα. 35 | —P(=O)(OCH$_2$—CH=CH—Cl)$_2$ |
| Iaα. 36 | —P(=O)(OCH$_2$—C≡CH$_2$)$_2$ |
| Iaα. 37 | —P(=O)[OCH(CH$_3$)—C≡CH]$_2$ |
| Iaα. 38 | —P(=O)(OCH$_2$—CO—OCH$_3$)$_2$ |
| Iaα. 39 | —P(=O)(OCH$_2$—CO—OC$_2$H$_5$)$_2$ |
| Iaα. 40 | —P(=O)[OCH(CH$_3$)—CO—OCH$_3$]$_2$ |
| Iaα. 41 | —P(=O)[OCH(CH$_3$)—CO—OC$_2$H$_5$]$_2$ |
| Iaα. 42 | —P(=O)(OCH$_2$—CO—NH$_2$)$_2$ |
| Iaα. 43 | —P(=O)(OCH$_2$—CO—NH—CH$_3$)$_2$ |
| Iaα. 44 | —P(=O)[OCH$_2$—CO—N(CH$_3$)$_2$]$_2$ |
| Iaα. 45 | —P(=O)[OCH(CH$_3$)—CO—NH$_2$]$_2$ |
| Iaα. 46 | —P(=O)[OCH(CH$_3$)—CO—NH—CH$_3$]$_2$ |
| Iaα. 47 | —P(=O)[OCH(CH$_3$)—CO—N(CH$_3$)$_2$]$_2$ |
| Iaα. 48 | —P(=O)(O-cyclopropyl)$_2$ |
| Iaα. 49 | —P(=O)(O-cyclobutyl)$_2$ |
| Iaα. 50 | —P(=O)(O-cyclopentyl)$_2$ |
| Iaα. 51 | —P(=O)(O-cyclohexyl)$_2$ |
| Iaα. 52 | —P(=O)(OCH$_2$-cyclopropyl)$_2$ |
| Iaα. 53 | —P(=O)(OCH$_2$-cyclobutyl)$_2$ |
| Iaα. 54 | —P(=O)(OCH$_2$-cyclopentyl)$_2$ |
| Iaα. 55 | —P(=O)(OCH$_2$-cyclohexyl)$_2$ |
| Iaα. 56 | —P(=O)(O-phenyl)$_2$ |
| Iaα. 57 | —P(=O)(OCH$_2$-phenyl)$_2$ |
| Iaα. 58 | —P(=O)(O-oxetan-3-yl)$_2$ |

TABLE 1-continued

Iaα

| No. | —P(=Y)($Z^1R^1$)($Z^2R^2$) |
|---|---|
| Iaα. 59 | —P(=O)(O-tetrahydrofuran-2-yl)$_2$ |
| Iaα. 60 | —P(=O)(O-tetrahydrofuran-3-yl)$_2$ |
| Iaα. 61 | —P(=O)(O-tetrahydropyran-2-yl)$_2$ |
| Iaα. 62 | —P(=O)(O-tetrahydropyran-3-yl)$_2$ |
| Iaα. 63 | —P(=O)(O-tetrahydropyran-4-yl)$_2$ |
| Iaα. 64 | —P(=O)(OCH$_2$-oxiran-2-yl)$_2$ |
| Iaα. 65 | —P(=O)(OCH$_2$-oxetan-3-yl)$_2$ |
| Iaα. 66 | —P(=O)(OCH$_2$-tetrahydrofuran-2-yl)$_2$ |
| Iaα. 67 | —P(=O)(OCH$_2$-tetrahydrofuran-3-yl)$_2$ |
| Iaα. 68 | —P(=O)(OCH$_2$-pyrrolidin-1-yl)$_2$ |
| Iaα. 69 | —P(=O)[OCH$_2$—(2-pyrrolidon-1-yl)]$_2$ |
| Iaα. 70 | —P(=O)(OCH$_2$-tetrahydropyran-2-yl)$_2$ |
| Iaα. 71 | —P(=O)(OCH$_2$-tetrahydropyran-3-yl)$_2$ |
| Iaα. 72 | —P(=O)(OCH$_2$-tetrahydropyran-4-yl)$_2$ |
| Iaα. 73 | —P(=O)(OCH$_2$-piperidin-1-yl)$_2$ |
| Iaα. 74 | —P(=O)(OCH$_2$-morpholin-4-yl)$_2$ |
| Iaα. 75 | —P(=O)(OH)(OCH$_3$) |
| Iaα. 76 | —P(=O)(OH)(OC$_2$H$_5$) |
| Iaα. 77 | —P(=O)(OH)[O—(n-C$_3$H$_7$)] |
| Iaα. 78 | —P(=O)(OH)[OCH(CH$_3$)$_2$] |
| Iaα. 79 | —P(=O)(OH)[O—(n-C$_4$H$_9$)] |
| Iaα. 80 | —P(=O)(OH)[OCH$_2$—CH(CH$_3$)$_2$] |
| Iaα. 81 | —P(=O)(OH)[OCH(CH$_3$)—C$_2$H$_5$] |
| Iaα. 82 | —P(=O)(OH)(OCH$_2$—CF$_3$) |
| Iaα. 83 | —P(=O)(OH)(OCH$_2$—CH$_2$—OH) |
| Iaα. 84 | —P(=O)(OH)(OCH$_2$—CH$_2$—CN) |
| Iaα. 85 | —P(=O)(OH)(OCH$_2$—CH$_2$—OCH$_3$) |
| Iaα. 86 | —P(=O)(OH)(OCH$_2$—CH$_2$—OC$_2$H$_5$) |
| Iaα. 87 | —P(=O)(OH)(OCH$_2$—CH$_2$—OCF$_3$) |
| Iaα. 88 | —P(=O)(OH)(OCH$_2$—CH$_2$—OCH$_2$—CH=CH$_2$) |
| Iaα. 89 | —P(=O)(OH)(OCH$_2$—CH$_2$—OCH$_2$—C≡CH) |
| Iaα. 90 | —P(=O)(OH)(OCH$_2$—CH$_2$—O-cyclopentyl) |
| Iaα. 91 | —P(=O)(OH)(OCH$_2$—CH$_2$—NH$_2$) |
| Iaα. 92 | —P(=O)(OH)(OCH$_2$—CH$_2$—NH—CH$_3$) |
| Iaα. 93 | —P(=O)(OH)[OCH$_2$—CH$_2$—N(CH$_3$)$_2$] |
| Iaα. 94 | —P(=O)(OH)(OCH$_2$—CH$_2$—SCH$_3$) |
| Iaα. 95 | —P(=O)(OH)(OCH$_2$—CH$_2$—SC$_2$H$_5$) |
| Iaα. 96 | —P(=O)(OH)(OCH$_2$—CH$_2$—SCF$_3$) |
| Iaα. 97 | —P(=O)(OH)(OCH$_2$—CH$_2$—SCH$_2$—CH=CH$_2$) |
| Iaα. 98 | —P(=O)(OH)(OCH$_2$—CH$_2$—SCH$_2$—C≡CH) |
| Iaα. 99 | —P(=O)(OH)(OCH$_2$—CH$_2$—SO—CH$_3$) |
| Iaα. 100 | —P(=O)(OH)(OCH$_2$—CH$_2$—SO—C$_2$H$_5$) |
| Iaα. 101 | —P(=O)(OH)(OCH$_2$—SO$_2$—CH$_3$) |
| Iaα. 102 | —P(=O)(OH)(OCH$_2$—SO$_2$—C$_2$H$_5$) |
| Iaα. 103 | —P(=O)(OH)(OCH$_2$—CH$_2$—SO$_2$—CH$_3$) |
| Iaα. 104 | —P(=O)(OH)(OCH$_2$—CH$_2$—SO$_2$—C$_2$H$_5$) |
| Iaα. 105 | —P(=O)(OH)(OCH$_2$—CH=CH$_2$) |
| Iaα. 106 | —P(=O)(OH)(OCH$_2$—CH=CH—CH$_3$) |
| Iaα. 107 | —P(=O)(OH)(OCH$_2$—CH$_2$—CH=CH$_2$) |
| Iaα. 108 | —P(=O)(OH)(OCH$_2$—CH=CH—Cl) |
| Iaα. 109 | —P(=O)(OH)(OCH$_2$—C≡CH) |
| Iaα. 110 | —P(=O)(OH)[OCH(CH$_3$)—C≡CH] |
| Iaα. 111 | —P(=O)(OH)(OCH$_2$—CO—OCH$_3$) |
| Iaα. 112 | —P(=O)(OH)(OCH$_2$—CO—OC$_2$H$_5$) |
| Iaα. 113 | —P(=O)(OH)[OCH(CH$_3$)—CO—OCH$_3$] |
| Iaα. 114 | —P(=O)(OH)[OCH(CH$_3$)—CO—OC$_2$H$_5$] |
| Iaα. 115 | —P(=O)(OH)(OCH$_2$—CO—NH$_2$) |
| Iaα. 116 | —P(=O)(OH)(OCH$_2$—CO—NH—CH$_3$) |
| Iaα. 117 | —P(=O)(OH)[OCH$_2$—CO—N(CH$_3$)$_2$] |
| Iaα. 118 | —P(=O)(OH)[OCH(CH$_3$)—CO—NH$_2$] |
| Iaα. 119 | —P(=O)(OH)[OCH(CH$_3$)—CO—NH—CH$_3$] |
| Iaα. 120 | —P(=O)(OH)[OCH(CH$_3$—CO—N(CH$_3$)$_2$] |
| Iaα. 121 | —P(=O)(OH)(O-cyclopropyl) |
| Iaα. 122 | —P(=O)(OH)(O-cyclobutyl) |
| Iaα. 123 | —P(=O)(OH)(O-cyclopentyl) |
| Iaα. 124 | —P(=O)(OH)(O-cyclohexyl) |

TABLE 1-continued

Iaα

| No. | —P(=Y)(Z$^1$R$^1$)(Z$^2$R$^2$) |
|---|---|
| Iaα. 125 | —P(=O)(OH)(OCH$_2$-cyclopropyl) |
| Iaα. 126 | —P(=O)(OH)(OCH$_2$-cyclobutyl) |
| Iaα. 127 | —P(=O)(OH)(OCH$_2$-cyclopentyl) |
| Iaα. 128 | —P(=O)(OH)(OCH$_2$-cyclohexyl) |
| Iaα. 129 | —P(=O)(OH)(O-phenyl) |
| Iaα. 130 | —P(=O)(OH)(OCH$_2$-phenyl) |
| Iaα. 131 | —P(=O)(OH)(O-oxetan-3-yl) |
| Iaα. 132 | —P(=O)(OH)(O-tetrahydrofuran-2-yl) |
| Iaα. 133 | —P(=O)(OH)(O-tetrahydrofuran-3-yl) |
| Iaα. 134 | —P(=O)(OH)(O-tetrahydropyran-2-yl) |
| Iaα. 135 | —P(=O)(OH)(O-tetrahydropyran-3-yl) |
| Iaα. 136 | —P(=O)(OH)(O-tetrahydropyran-4-yl) |
| Iaα. 137 | —P(=O)(OH)(OCH$_2$-oxiran-2-yl) |
| Iaα. 138 | —P(=O)(OH)(OCH$_2$-oxetan-3-yl) |
| Iaα. 139 | —P(=O)(OH)(OCH$_2$-tetrahydrofuran-2-yl) |
| Iaα. 140 | —P(=O)(OH)(OCH$_2$-tetrahydrofuran-3-yl) |
| Iaα. 141 | —P(=O)(OH)(OCH$_2$-pyrrolidin-1-yl) |
| Iaα. 142 | —P(=O)(OH)[OCH$_2$—(2-pyrrolidon-1-yl)] |
| Iaα. 143 | —P(=O)(OH)(OCH$_2$-tetrahydropyran-2-yl) |
| Iaα. 144 | —P(=O)(OH)(OCH$_2$-tetrahydropyran-3-yl) |
| Iaα. 145 | —P(=O)(OH)(OCH$_2$-tetrahydropyran-4-yl) |
| Iaα. 146 | —P(=O)(OH)(OCH$_2$-piperidin-1-yl) |
| Iaα. 147 | —P(=O)(OH)(OCH$_2$-morpholin-4-yl) |
| Iaα. 148 | —P(=O)(OCH$_3$)(OC$_2$H$_5$) |
| Iaα. 149 | —P(=O)(OCH$_3$)[O—(n-C$_3$H$_7$)] |
| Iaα. 150 | —P(=O)(OCH$_3$)[OCH(CH$_3$)$_2$] |
| Iaα. 151 | —P(=O)(OCH$_3$)[O—(n-C$_4$H$_9$)] |
| Iaα. 152 | —P(=O)(OCH$_3$)[OCH$_2$—CH(CH$_3$)$_2$] |
| Iaα. 153 | —P(=O)(OCH$_3$)[OCH(CH$_3$)—C$_2$H$_5$] |
| Iaα. 154 | —P(=O)(OCH$_3$)(OCH$_2$—CF$_3$) |
| Iaα. 155 | —P(=O)(OCH$_3$)(OCH$_2$—CH$_2$—OH) |
| Iaα. 156 | —P(=O)(OCH$_3$)(OCH$_2$—CH$_2$—CN) |
| Iaα. 157 | —P(=O)(OCH$_3$)(OCH$_2$—CH$_2$—OCH$_3$) |
| Iaα. 158 | —P(=O)(OCH$_3$)(OCH$_2$—CH$_2$—OC$_2$H$_5$) |
| Iaα. 159 | —P(=O)(OCH$_3$)(OCH$_2$—CH$_2$—OCF$_3$) |
| Iaα. 160 | —P(=O)(OCH$_3$)(OCH$_2$—CH$_2$—OCH$_2$—CH=CH$_2$) |
| Iaα. 161 | —P(=O)(OCH$_3$)(OCH$_2$—CH$_2$—OCH$_2$—C≡CH) |
| Iaα. 162 | —P(=O)(OCH$_3$)(OCH$_2$—CH$_2$—O-cyclopentyl) |
| Iaα. 163 | —P(=O)(OCH$_3$)(OCH$_2$—CH$_2$—NH$_2$) |
| Iaα. 164 | —P(=O)(OCH$_3$)(OCH$_2$—CH$_2$—NH—CH$_3$) |
| Iaα. 165 | —P(=O)(OCH$_3$)[OCH$_2$—CH$_2$—N(CH$_3$)$_2$] |
| Iaα. 166 | —P(=O)(OCH$_3$)(OCH$_2$—CH$_2$—SCH$_3$) |
| Iaα. 167 | —P(=O)(OCH$_3$)(OCH$_2$—CH$_2$—SC$_2$H$_5$) |
| Iaα. 168 | —P(=O)(OCH$_3$)(OCH$_2$—CH$_2$—SCF$_3$) |
| Iaα. 169 | —P(=O)(OCH$_3$)(OCH$_2$—CH$_2$—SCH$_2$—CH=CH$_2$) |
| Iaα. 170 | —P(=O)(OCH$_3$)(OCH$_2$—CH$_2$—SCH$_2$—C≡CH) |
| Iaα. 171 | —P(=O)(OCH$_3$)(OCH$_2$—CH$_2$—SO—CH$_3$) |
| Iaα. 172 | —P(=O)(OCH$_3$)(OCH$_2$—CH$_2$—SO—C$_2$H$_5$) |
| Iaα. 173 | —P(=O)(OCH$_3$)(OCH$_2$—SO$_2$—CH$_3$) |
| Iaα. 174 | —P(=O)(OCH$_3$)(OCH$_2$—SO$_2$—C$_2$H$_5$) |
| Iaα. 175 | —P(=O)(OCH$_3$)(OCH$_2$—CH$_2$—SO$_2$—CH$_3$) |
| Iaα. 176 | —P(=O)(OCH$_3$)(OCH$_2$—CH$_2$—SO$_2$—C$_2$H$_5$) |
| Iaα. 177 | —P(=O)(OCH$_3$)(OCH$_2$—CH=CH$_2$) |
| Iaα. 178 | —P(=O)(OCH$_3$)(OCH$_2$—CH=CH—CH$_3$) |
| Iaα. 179 | —P(=O)(OCH$_3$)(OCH$_2$—CH$_2$—CH=CH$_2$) |
| Iaα. 180 | —P(=O)(OCH$_3$)(OCH$_2$—CH=CH—Cl) |
| Iaα. 181 | —P(=O)(OCH$_3$)(OCH$_2$—C≡CH) |
| Iaα. 182 | —P(=O)(OCH$_3$)[OCH(CH$_3$)—C≡CH] |
| Iaα. 183 | —P(=O)(OCH$_3$)(OCH$_2$—CO—OCH$_3$) |
| Iaα. 184 | —P(=O)(OCH$_3$)(OCH$_2$—CO—OC$_2$H$_5$) |
| Iaα. 185 | —P(=O)(OCH$_3$)[OCH(CH$_3$)—CO—OCH$_3$] |
| Iaα. 186 | —P(=O)(OCH$_3$)[OCH(CH$_3$)—CO—OC$_2$H$_5$] |
| Iaα. 187 | —P(=O)(OCH$_3$)(OCH$_2$—CO—NH$_2$) |
| Iaα. 188 | —P(=O)(OCH$_3$)(OCH$_2$—CO—NH—CH$_3$) |
| Iaα. 189 | —P(=O)(OCH$_3$)(OCH$_2$—CO—N(CH$_3$)$_2$) |
| Iaα. 190 | —P(=O)(OCH$_3$)[OCH(CH$_3$)—CO—NH$_2$] |
| Iaα. 191 | —P(=O)(OCH$_3$)[OCH(CH$_3$)—CO—NH—CH$_3$] |
| Iaα. 192 | —P(=O)(OCH$_3$)[OCH(CH$_3$)—CO—N(CH$_3$)$_2$] |
| Iaα. 193 | —P(=O)(OCH$_3$)(O-cyclopropyl) |
| Iaα. 194 | —P(=O)(OCH$_3$)(O-cyclobutyl) |
| Iaα. 195 | —P(=O)(OCH$_3$)(O-cyclopentyl) |
| Iaα. 196 | —P(=O)(OCH$_3$)(O-cyclohexyl) |
| Iaα. 197 | —P(=O)(OCH$_3$)(OCH$_2$-cyclopropyl) |
| Iaα. 198 | —P(=O)(OCH$_3$)(OCH$_2$-cyclobutyl) |
| Iaα. 199 | —P(=O)(OCH$_3$)(OCH$_2$-cyclopentyl) |
| Iaα. 200 | —P(=O)(OCH$_3$)(OCH$_2$-cyclohexyl) |
| Iaα. 201 | —P(=O)(OCH$_3$)(O-phenyl) |
| Iaα. 202 | —P(=O)(OCH$_3$)(OCH$_2$-phenyl) |
| Iaα. 203 | —P(=O)(OCH$_3$)(O-oxetan-3-yl) |
| Iaα. 204 | —P(=O)(OCH$_3$)(O-tetrahydrofuran-2-yl) |
| Iaα. 205 | —P(=O)(OCH$_3$)(O-tetrahydrofuran-3-yl) |
| Iaα. 206 | —P(=O)(OCH$_3$)(O-tetrahydropyran-2-yl) |
| Iaα. 207 | —P(=O)(OCH$_3$)(O-tetrahydropyran-3-yl) |
| Iaα. 208 | —P(=O)(OCH$_3$)(O-tetrahydropyran-4-yl) |
| Iaα. 209 | —P(=O)(OCH$_3$)(OCH$_2$-oxiran-2-yl) |
| Iaα. 210 | —P(=O)(OCH$_3$)(OCH$_2$-oxetan-3-yl) |
| Iaα. 211 | —P(=O)(OCH$_3$)(OCH$_2$-tetrahydrofuran-2-yl) |
| Iaα. 212 | —P(=O)(OCH$_3$)(OCH$_2$-tetrahydrofuran-3-yl) |
| Iaα. 213 | —P(=O)(OCH$_3$)(OCH$_2$-pyrrolidin-1-yl) |
| Iaα. 214 | —P(=O)(OCH$_3$)[OCH$_2$—(2-pyrrolidon-1-yl)] |
| Iaα. 215 | —P(=O)(OCH$_3$)(OCH$_2$-tetrahydropyran-2-yl) |
| Iaα. 216 | —P(=O)(OCH$_3$)(OCH$_2$-tetrahydropyran-3-yl) |
| Iaα. 217 | —P(=O)(OCH$_3$)(OCH$_2$-tetrahydropyran-4-yl) |
| Iaα. 218 | —P(=O)(OCH$_3$)(OCH$_2$-piperidin-1-yl) |
| Iaα. 219 | —P(=O)(OCH$_3$)(OCH$_2$-morpholin-4-yl) |
| Iaα. 220 | —P(=O)(OC$_2$H$_5$)[O—(n-C$_3$H$_7$)] |
| Iaα. 221 | —P(=O)(OC$_2$H$_5$)[OCH(CH$_3$)$_2$] |
| Iaα. 222 | —P(=O)(OC$_2$H$_5$)[O—(n-C$_4$H$_9$)] |
| Iaα. 223 | —P(=O)(OC$_2$H$_5$)[OCH$_2$—CH(CH$_3$)$_2$] |
| Iaα. 224 | —P(=O)(OC$_2$H$_5$)[OCH(CH$_3$)—C$_2$H$_5$] |
| Iaα. 225 | —P(=O)(OC$_2$H$_5$)(OCH$_2$—CF$_3$) |
| Iaα. 226 | —P(=O)(OC$_2$H$_5$)(OCH$_2$—CH$_2$—OH) |
| Iaα. 227 | —P(=O)(OC$_2$H$_5$)(OCH$_2$—CH$_2$—CN) |
| Iaα. 228 | —P(=O)(OC$_2$H$_5$)(OCH$_2$—CH$_2$—OCH$_3$) |
| Iaα. 229 | —P(=O)(OC$_2$H$_5$)(OCH$_2$—CH$_2$—OC$_2$H$_5$) |
| Iaα. 230 | —P(=O)(OC$_2$H$_5$)(OCH$_2$—CH$_2$—OCF$_3$) |
| Iaα. 231 | —P(=O)(OC$_2$H$_5$)(OCH$_2$—CH$_2$—OCH$_2$—CH=CH$_2$) |
| Iaα. 232 | —P(=O)(OC$_2$H$_5$)(OCH$_2$—CH$_2$—OCH$_2$—C≡CH) |
| Iaα. 233 | —P(=O)(OC$_2$H$_5$)(OCH$_2$—CH$_2$—O-cyclopentyl) |
| Iaα. 234 | —P(=O)(OC$_2$H$_5$)(OCH$_2$—CH$_2$—NH$_2$) |
| Iaα. 235 | —P(=O)(OC$_2$H$_5$)(OCH$_2$—CH$_2$—NH—CH$_3$) |
| Iaα. 236 | —P(=O)(OC$_2$H$_5$)[OCH$_2$—CH$_2$—N(CH$_3$)$_2$] |
| Iaα. 237 | —P(=O)(OC$_2$H$_5$)(OCH$_2$—CH$_2$—SCH$_3$) |
| Iaα. 238 | —P(=O)(OC$_2$H$_5$)(OCH$_2$—CH$_2$—SC$_2$H$_5$) |
| Iaα. 239 | —P(=O)(OC$_2$H$_5$)(OCH$_2$—CH$_2$—SCF$_3$) |
| Iaα. 240 | —P(=O)(OC$_2$H$_5$)(OCH$_2$—CH$_2$—SCH$_2$—CH=CH$_2$) |
| Iaα. 241 | —P(=O)(OC$_2$H$_5$)(OCH$_2$—CH$_2$—SCH$_2$—C≡CH) |
| Iaα. 242 | —P(=O)(OC$_2$H$_5$)(OCH$_2$—CH$_2$—SO—CH$_3$) |
| Iaα. 243 | —P(=O)(OC$_2$H$_5$)(OCH$_2$—CH$_2$—SO—C$_2$H$_5$) |
| Iaα. 244 | —P(=O)(OC$_2$H$_5$)(OCH$_2$—SO$_2$—CH$_3$) |
| Iaα. 245 | —P(=O)(OC$_2$H$_5$)(OCH$_2$—SO$_2$—C$_2$H$_5$) |
| Iaα. 246 | —P(=O)(OC$_2$H$_5$)(OCH$_2$—CH$_2$—SO$_2$—CH$_3$) |
| Iaα. 247 | —P(=O)(OC$_2$H$_5$)(OCH$_2$—CH$_2$—SO$_2$—C$_2$H$_5$) |
| Iaα. 248 | —P(=O)(OC$_2$H$_5$)(OCH$_2$—CH=CH$_2$) |
| Iaα. 249 | —P(=O)(OC$_2$H$_5$)(OCH$_2$—CH=CH—CH$_3$) |
| Iaα. 250 | —P(=O)(OC$_2$H$_5$)(OCH$_2$—CH$_2$—CH=CH$_2$) |
| Iaα. 251 | —P(=O)(OC$_2$H$_5$)(OCH$_2$—CH=CH—Cl) |
| Iaα. 252 | —P(=O)(OC$_2$H$_5$)(OCH$_2$—C≡CH) |
| Iaα. 253 | —P(=O)(OC$_2$H$_5$)[OCH(CH$_3$)—C≡CH] |
| Iaα. 254 | —P(=O)(OC$_2$H$_5$)(OCH$_2$—CO—OCH$_3$) |
| Iaα. 255 | —P(=O)(OC$_2$H$_5$)(OCH$_2$—CO—OC$_2$H$_5$) |
| Iaα. 256 | —P(=O)(OC$_2$H$_5$)[OCH(CH$_3$)—CO—OCH$_3$] |

TABLE 1-continued

Iaα

| No. | —P(=Y)(Z$^1$R$^1$)(Z$^2$R$^2$) |
|---|---|
| Iaα. 257 | —P(=O)(OC$_2$H$_5$)[OCH(CH$_3$)—CO—OC$_2$H$_5$] |
| Iaα. 258 | —P(=O)(OC$_2$H$_5$)(OCH$_2$—CO—NH$_2$) |
| Iaα. 259 | —P(=O)(OC$_2$H$_5$)(OCH$_2$—CO—NH—CH$_3$) |
| Iaα. 260 | —P(=O)(OC$_2$H$_5$)[OCH$_2$—CO—N(CH$_3$)$_2$] |
| Iaα. 261 | —P(=O)(OC$_2$H$_5$)[OCH(CH$_3$)—CO—NH$_2$] |
| Iaα. 262 | —P(=O)(OC$_2$H$_5$)[OCH(CH$_3$)—CO—NH—CH$_3$] |
| Iaα. 263 | —P(=O)(OC$_2$H$_5$)[OCH(CH$_3$)—CO—N(CH$_3$)$_2$] |
| Iaα. 264 | —P(=O)(OC$_2$H$_5$)(O-cyclopropyl) |
| Iaα. 265 | —P(=O)(OC$_2$H$_5$)(O-cyclobutyl) |
| Iaα. 266 | —P(=O)(OC$_2$H$_5$)(O-cyclopentyl) |
| Iaα. 267 | —P(=O)(OC$_2$H$_5$)(O-cyclohexyl) |
| Iaα. 268 | —P(=O)(OC$_2$H$_5$)(OCH$_2$-cyclopropyl) |
| Iaα. 269 | —P(=O)(OC$_2$H$_5$)(OCH$_2$-cyclobutyl) |
| Iaα. 270 | —P(=O)(OC$_2$H$_5$)(OCH$_2$-cyclopentyl) |
| Iaα. 271 | —P(=O)(OC$_2$H$_5$)(OCH$_2$-cyclohexyl) |
| Iaα. 272 | —P(=O)(OC$_2$H$_5$)(O-phenyl) |
| Iaα. 273 | —P(=O)(OC$_2$H$_5$)(OCH$_2$-phenyl) |
| Iaα. 274 | —P(=O)(OC$_2$H$_5$)(O-oxetan-3-yl) |
| Iaα. 275 | —P(=O)(OC$_2$H$_5$)(O-tetrahydrofuran-2-yl) |
| Iaα. 276 | —P(=O)(OC$_2$H$_5$)(O-tetrahydrofuran-3-yl) |
| Iaα. 277 | —P(=O)(OC$_2$H$_5$)(O-tetrahydropyran-2-yl) |
| Iaα. 278 | —P(=O)(OC$_2$H$_5$)(O-tetrahydropyran-3-yl) |
| Iaα. 279 | —P(=O)(OC$_2$H$_5$)(O-tetrahydropyran-4-yl) |
| Iaα. 280 | —P(=O)(OC$_2$H$_5$)(OCH$_2$-oxiran-2-yl) |
| Iaα. 281 | —P(=O)(OC$_2$H$_5$)(OCH$_2$-oxetan-3-yl) |
| Iaα. 282 | —P(=O)(OC$_2$H$_5$)(OCH$_2$-tetrahydrofuran-2-yl) |
| Iaα. 283 | —P(=O)(OC$_2$H$_5$)(OCH$_2$-tetrahydrofuran-3-yl) |
| Iaα. 284 | —P(=O)(OC$_2$H$_5$)(OCH$_2$-pyrrolidin-1-yl) |
| Iaα. 285 | —P(=O)(OC$_2$H$_5$)[OCH$_2$—(2-pyrrolidon-1-yl)] |
| Iaα. 286 | —P(=O)(OC$_2$H$_5$)(OCH$_2$-tetrahydropyran-2-yl) |
| Iaα. 287 | —P(=O)(OC$_2$H$_5$)(OCH$_2$-tetrahydropyran-3-yl) |
| Iaα. 288 | —P(=O)(OC$_2$H$_5$)(OCH$_2$-tetrahydropyran-4-yl) |
| Iaα. 289 | —P(=O)(OC$_2$H$_5$)(OCH$_2$-piperidin-1-yl) |
| Iaα. 290 | —P(=O)(OC$_2$H$_5$)(OCH$_2$-morpholin-4-yl) |
| Iaα. 291 | —P(=O)(1,2-phenylenedioxy) |
| Iaα. 292 | —P(=O)(O—CH$_2$—CH$_2$—O) |
| Iaα. 293 | —P(=O)[O—CH(CH$_3$)—CH$_2$—O] |
| Iaα. 294 | —P(=O)[O—CH(CH$_3$)—CH(CH$_3$)—O] |
| Iaα. 295 | —P(=O)[O—CH(COOCH$_3$)—CH(COOCH$_3$)—O] |
| Iaα. 296 | —P(=O)(O—CH$_2$—CH$_2$—CH$_2$—O) |
| Iaα. 297 | —P(=O)[O—CH$_2$—C(CH$_3$)$_2$—CH$_2$—O] |
| Iaα. 298 | —P(=O)(O—CH$_2$—CH$_2$—CH$_2$—CH$_2$—O) |
| Iaα. 299 | —P(=S)(OH)$_2$ |
| Iaα. 300 | —P(=S)(OCH$_3$)$_2$ |
| Iaα. 301 | —P(=S)(OC$_2$H$_5$)$_2$ |
| Iaα. 302 | —P(=S)[O—(n-C$_3$H$_7$)]$_2$ |
| Iaα. 303 | —P(=S)[O—(n-C$_4$H$_9$)]$_2$ |
| Iaα. 304 | —P(=S)(O—CH$_2$—CH$_2$—CH$_2$—O) |
| Iaα. 305 | —P(=O)(NH$_2$)$_2$ |
| Iaα. 306 | —P(=O)(NH—CH$_3$)$_2$ |
| Iaα. 307 | —P(=O)[N(CH$_3$)$_2$]$_2$ |
| Iaα. 308 | —P(=O)(NH—C$_2$H$_5$)$_2$ |
| Iaα. 309 | —P(=O)[N(C$_2$H$_5$)$_2$]$_2$ |
| Iaα. 310 | —P(=O)(NH—CH$_2$—CH=CH$_2$)$_2$ |
| Iaα. 311 | —P(=O)(NH—CH$_2$—C≡CH)$_2$ |
| Iaα. 312 | —P(=O)(NH-cyclopropyl)$_2$ |
| Iaα. 313 | —P(=O)(NH—CH$_2$-cyclopentyl)$_2$ |
| Iaα. 314 | —P(=O)(NH-phenyl)$_2$ |
| Iaα. 315 | —P(=O)(NH—CH$_2$-phenyl)$_2$ |
| Iaα. 316 | —P(=O)(pyrrolidin-1-yl)$_2$ |
| Iaα. 317 | —P(=O)(2-methoxycarbonylpyrrolidin-1-yl)$_2$ |
| Iaα. 318 | —P(=O)(NH—CH$_2$—CO—OCH$_3$)$_2$ |
| Iaα. 319 | —P(=O)[N(CH$_3$)—CH$_2$—CO—OCH$_3$]$_2$ |
| Iaα. 320 | —P(=O)(NH—CH$_2$—CO—OC$_2$H$_5$)$_2$ |
| Iaα. 321 | —P(=O)[N(CH$_3$)—CH$_2$—CO—OC$_2$H$_5$]$_2$ |
| Iaα. 322 | —P(=O)[NH—CH(CH$_3$)—CO—OCH$_3$]$_2$ |
| Iaα. 323 | —P(=O)(OH)(NH$_2$) |
| Iaα. 324 | —P(=O)(OH)(NH—CH$_3$) |
| Iaα. 325 | —P(=O)(OH)[N(CH$_3$)$_2$] |
| Iaα. 326 | —P(=O)(OH)(NH—C$_2$H$_5$) |
| Iaα. 327 | —P(=O)(OH)[N(C$_2$H$_5$)$_2$] |
| Iaα. 328 | —P(=O)(OH)(NH—CH$_2$—CH=CH$_2$) |
| Iaα. 329 | —P(=O)(OH)(NH—CH$_2$—C≡CH) |
| Iaα. 330 | —P(=O)(OH)(NH-cyclopropyl) |
| Iaα. 331 | —P(=O)(OH)(NH—CH$_2$-cyclopentyl) |
| Iaα. 332 | —P(=O)(OH)(NH-phenyl) |
| Iaα. 333 | —P(=O)(OH)(NH—CH$_2$-phenyl) |
| Iaα. 334 | —P(=O)(OH)(pyrrolidin-1-yl) |
| Iaα. 335 | —P(=O)(OH)(2-methoxycarbonylpyrrolidin-1-yl) |
| Iaα. 336 | —P(=O)(OH)(NH—CH$_2$—CO—OCH$_3$) |
| Iaα. 337 | —P(=O)(OH)[N(CH$_3$)—CH$_2$—CO—OCH$_3$] |
| Iaα. 338 | —P(=O)(OH)(NH—CH$_2$—CO—OC$_2$H$_5$) |
| Iaα. 339 | —P(=O)(OH)[N(CH$_3$)—CH$_2$—CO—OC$_2$H$_5$] |
| Iaα. 340 | —P(=O)(OH)[NH—CH(CH$_3$)—CO—OCH$_3$] |
| Iaα. 341 | —P(=O)(OCH$_3$)(NH$_2$) |
| Iaα. 342 | —P(=O)(OCH$_3$)(NH—CH$_3$) |
| Iaα. 343 | —P(=O)(OCH$_3$)[N(CH$_3$)$_2$] |
| Iaα. 344 | —P(=O)(OCH$_3$)(NH—C$_2$H$_5$) |
| Iaα. 345 | —P(=O)(OCH$_3$)[N(C$_2$H$_5$)$_2$] |
| Iaα. 346 | —P(=O)(OCH$_3$)(NH—CH$_2$—CH=CH$_2$) |
| Iaα. 347 | —P(=O)(OCH$_3$)(NH—CH$_2$—C≡CH) |
| Iaα. 348 | —P(=O)(OCH$_3$)(NH-cyclopropyl) |
| Iaα. 349 | —P(=O)(OCH$_3$)(NH—CH$_2$-cyclopentyl) |
| Iaα. 350 | —P(=O)(OCH$_3$)(NH-phenyl) |
| Iaα. 351 | —P(=O)(OCH$_3$)(NH—CH$_2$-phenyl) |
| Iaα. 352 | —P(=O)(OCH$_3$)(pyrrolidin-1-yl) |
| Iaα. 353 | —P(=O)(OCH$_3$)(2-methoxycarbonylpyrrolidin-1-yl) |
| Iaα. 354 | —P(=O)(OCH$_3$)(NH—CH$_2$—CO—OCH$_3$) |
| Iaα. 355 | —P(=O)(OCH$_3$)[N(CH$_3$)—CH$_2$—CO—OCH$_3$] |
| Iaα. 356 | —P(=O)(OCH$_3$)(NH—CH$_2$—CO—OC$_2$H$_5$) |
| Iaα. 357 | —P(=O)(OCH$_3$)[N(CH$_3$)—CH$_2$—CO—OC$_2$H$_5$] |
| Iaα. 358 | —P(=O)(OCH$_3$)[NH—CH(CH$_3$)—CO—OCH$_3$] |
| Iaα. 359 | —P(=O)(OC$_2$H$_5$)(NH$_2$) |
| Iaα. 360 | —P(=O)(OC$_2$H$_5$)(NH—CH$_3$) |
| Iaα. 361 | —P(=O)(OC$_2$H$_5$)[N(CH$_3$)$_2$] |
| Iaα. 362 | —P(=O)(OC$_2$H$_5$)(NH—C$_2$H$_5$) |
| Iaα. 363 | —P(=O)(OC$_2$H$_5$)[N(C$_2$H$_5$)$_2$] |
| Iaα. 364 | —P(=O)(OC$_2$H$_5$)(NH—CH$_2$—CH=CH$_2$) |
| Iaα. 365 | —P(=O)(OC$_2$H$_5$)(NH—CH$_2$—C≡CH) |
| Iaα. 366 | —P(=O)(OC$_2$H$_5$)(NH-cyclopropyl) |
| Iaα. 367 | —P(=O)(OC$_2$H$_5$)(NH—CH$_2$-cyclopentyl) |
| Iaα. 368 | —P(=O)(OC$_2$H$_5$)(NH-phenyl) |
| Iaα. 369 | —P(=O)(OC$_2$H$_5$)(NH—CH$_2$-phenyl) |
| Iaα. 370 | —P(=O)(OC$_2$H$_5$)(pyrrolidin-1-yl) |
| Iaα. 371 | —P(=O)(OC$_2$H$_5$)(2-methoxycarbonylpyrrolidin-1-yl) |
| Iaα. 372 | —P(=O)(OC$_2$H$_5$)(NH—CH$_2$—CO—OCH$_3$) |
| Iaα. 373 | —P(=O)(OC$_2$H$_5$)[N(CH$_3$)—CH$_2$—CO—OCH$_3$] |
| Iaα. 374 | —P(=O)(OC$_2$H$_5$)(NH—CH$_2$—CO—OC$_2$H$_5$) |
| Iaα. 375 | —P(=O)(OC$_2$H$_5$)[N(CH$_3$)—CH$_2$—CO—OC$_2$H$_5$] |
| Iaα. 376 | —P(=O)(OC$_2$H$_5$)[NH—CH(CH$_3$)—CO—OCH$_3$] |
| Iaα. 377 | —P(=O)[N(CH$_3$)$_2$](OCH$_3$) |
| Iaα. 378 | —P(=O)[N(CH$_3$)$_2$](OC$_2$H$_5$) |
| Iaα. 379 | —P(=O)[N(CH$_3$)$_2$][O—(n-C$_3$H$_7$)] |
| Iaα. 380 | —P(=O)[N(CH$_3$)$_2$][OCH(CH$_3$)$_2$] |
| Iaα. 381 | —P(=O)[N(CH$_3$)$_2$][O—(n-C$_4$H$_9$)] |
| Iaα. 382 | —P(=O)[N(CH$_3$)$_2$](OCH$_2$—CH=CH$_2$) |
| Iaα. 383 | —P(=O)[N(CH$_3$)$_2$](OCH$_2$—C≡CH) |
| Iaα. 384 | —P(=O)[N(CH$_3$)$_2$](O-cyclohexyl) |
| Iaα. 385 | —P(=O)[N(CH$_3$)$_2$](OCH$_2$-cyclohexyl) |
| Iaα. 386 | —P(=O)[N(CH$_3$)$_2$](O-phenyl) |
| Iaα. 387 | —P(=O)[N(CH$_3$)$_2$](OCH$_2$-phenyl) |
| Iaα. 388 | —P(=O)[N(CH$_3$)$_2$](O-tetrahydrofuran-2-yl) |

TABLE 1-continued

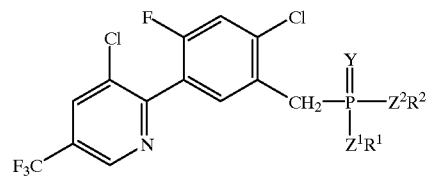

Iaα

| No. | —P(=Y)(Z¹R¹)(Z²R²) |
|---|---|
| Iaα. 389 | —P(=O)[N(CH₃)₂](OCH₂-oxetan-3-yl) |
| Iaα. 390 | —P(=O)[N(CH₃)₂](OCH₂—CF₃) |
| Iaα. 391 | —P(=O)[N(CH₃)₂](OCH₂—CO—OCH₃) |
| Iaα. 392 | —P(=O)[N(CH₃)₂](OCH₂—CO—OC₂H₅) |
| Iaα. 393 | —P(=O)(NH—CH₂—CH₂—O) |
| Iaα. 394 | —P(=O)(NH—CH₂—CH₂—NH) |
| Iaα. 395 | —P(=O)[N(CH₃)—CH₂—CH₂—N(CH₃)] |
| Iaα. 396 | —P(=O)(NH—CH₂—CH₂—CH₂—O) |
| Iaα. 397 | —P(=O)(NH—CH₂—CH₂—CH₂—NH) |
| Iaα. 398 | —P(=O)[N(CH₃)—CH₂—CH₂—CH₂—N(CH₃)] |
| Iaα. 399 | —P(=O)[O—CH₂—CH(CH₃)—CH₂—O] |
| Iaα. 400 | —P(=O)[NH—CH₂—CH₂—CH₂—N(CH₃] |
| Iaα. 401 | —P(=O)[N(CH₃)—CH₂—C(CH₃)₂—CH₂—N(CH₃] |
| Iaα. 402 | —P(=O)[NH—CH₂—CH₂—CH₂—CH₂—O] |
| Iaα. 403 | —P(=O)[NH—CH₂—CH₂—CH₂—CH₂—NH] |
| Iaα. 404 | —P(=S)(NH₂)₂ |
| Iaα. 405 | —P(=S)(NH—CH₃)₂ |
| Iaα. 406 | —P(=S)[N(CH₃)₂]₂ |
| Iaα. 407 | —P(=S)(NH—C₂H₅)₂ |
| Iaα. 408 | —P(=S)[N(C₂H₅)₂]₂ |
| Iaα. 409 | —P(=S)(NH—CH₂—CH₂—CH₂—O) |
| Iaα. 410 | —P(=S)(NH—CH₂—CH₂—CH₂—NH) |
| Iaα. 411 | —P(=S)[N(CH₃)—CH₂—CH₂—CH₂—N(CH₃)] |
| Iaα. 412 | —P(=O)(SCH₃)₂ |
| Iaα. 413 | —P(=O)(SC₂H₅)₂ |
| Iaα. 414 | —P(=O)[S—(n-C₃H₇)]₂ |
| Iaα. 415 | —P(=O)[SCH(CH₃)₂]₂ |
| Iaα. 416 | —P(=O)[S—(n-C₄H₉)]₂ |
| Iaα. 417 | —P(=O)(SCH₂—CH=CH₂)₂ |
| Iaα. 418 | —P(=O)(S-phenyl)₂ |
| Iaα. 419 | —P(=O)(SCH₂-phenyl)₂ |
| Iaα. 420 | —P(=O)(SCH₂—CO—OCH₃)₂ |
| Iaα. 421 | —P(=O)(SCH₂—CO—OC₂H₅)₂ |
| Iaα. 422 | —P(=O)(S—CH₂—CH₂—CH₂—S) |
| Iaα. 423 | —P(=O)(S—CH₂—CH₂—CH₂—O) |
| Iaα. 424 | —P(=S)(SCH₃)₂ |
| Iaα. 425 | —P(=S)(SC₂H₅)₂ |
| Iaα. 426 | —P(=S)[S—(n-C₃H₇)]₂ |
| Iaα. 427 | —P(=S)[S-n-C₄H₉)]₂ |
| Iaα. 428 | —P(=S)(S—CH₂—CH₂—CH₂—S) |
| Iaα. 429 | —P(=S)(S—CH₂—CH₂—CH₂—O) |

Furthermore, the following substituted 2-phenylpyridines of the formulae Iaβ-Ioγ are especially preferred, in particular the compounds Iaβ.1–Iaβ.429, which differ from the corresponding compounds Iaα. 1–Iaα.429 only by the fact that $R^4$ is chlorine:

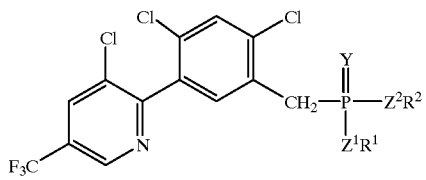

Iaβ the compounds Iaγ.1–Iaγ.429, which differ from the corresponding compounds Iaα. 1–Iaα.429 only by the fact that $R^4$ is fluorine:

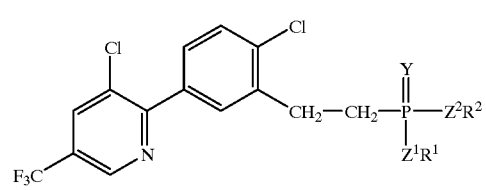

Iaγ the compounds Ibα.1–Ibα.429, which differ from the corresponding compounds Iaα.1–Iaα.429 only by the fact that X is 1,2-ethanediyl:

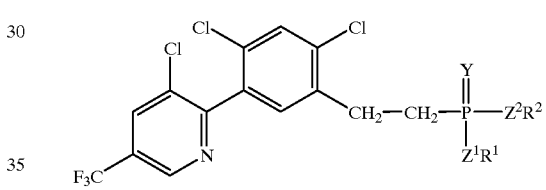

Ibα the compounds Ibβ.1–Ibβ.429, which differ from the corresponding compounds Iaα.1–Iaα.429 only by the fact that X is 1,2-ethanediyl and $R^4$ is chlorine:

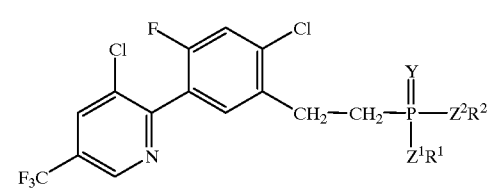

Ibβ the compounds Ibγ.1–Ibγ.429, which differ from the corresponding compounds Iaα.1–Iaα.429 only by the fact that X is 1,2-ethanediyl and $R^4$ is fluorine:

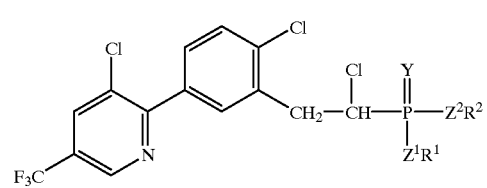

Ibγ the compounds Icα.1–Icα.429, which differ from the corresponding compounds Iaα.1–Iaα.429 only by the fact that X is —CH₂—CH(Cl)—:

Icα the compounds Icβ.1–Icβ.429, which differ from the corresponding compounds Iaα.1–Iaα.429 only by the fact that X is —CH₂—CH(Cl)— and $R^4$ is chlorine:

Icβ

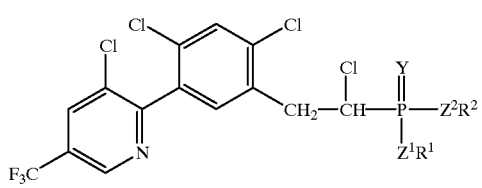

the compounds Icγ.1–Icγ. 429, which differ from the corresponding compounds Iaα.1–Iaα.429 only by the fact that X is —CH$_2$—CH(Cl)— and R$^4$ is fluorine:

Icγ

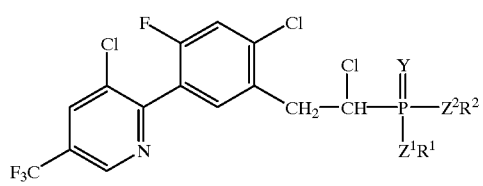

the compounds Idα.1–Idα. 429, which differ from the corresponding compounds Iaα.1–Iaα.429 only by the fact that X is —CH$_2$—CH(Br)—:

Idα

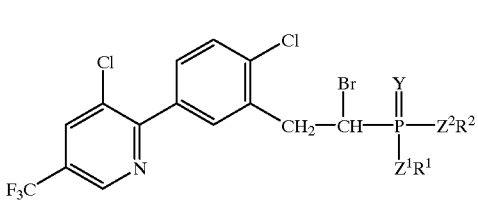

the compounds Idβ.1–Idβ.429, which differ from the corresponding compounds Iaα.1–Iaα.429 only by the fact that X is —CH$_2$—CH(Br)— and R$^4$ is chlorine:

Idβ

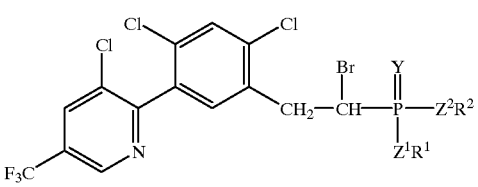

the compounds Idγ.1–Idγ.429, which differ from the corresponding compounds Iaα.1–Iaα.429 only by the fact that X is —CH$_2$—CH(Br)— and R$^4$ is fluorine:

Idγ

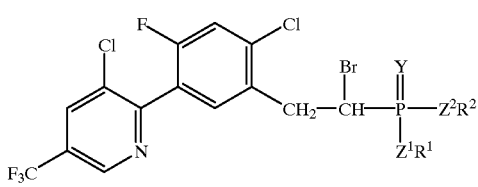

the compounds Ieα.1–Ieα.429, which differ from the corresponding compounds Iaα.1–Iaα.429 only by the fact that X is —CH$_2$—CH(CH$_3$)—:

Ieα

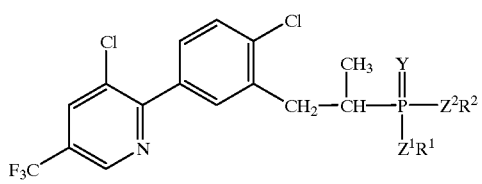

the compounds Ieβ.1–Ieβ.429, which differ from the corresponding compounds Iaα.1–Iaα.429 only by the fact that X is —CH$_2$—CH(CH$_3$)— and R$^4$ is chlorine:

Ieβ

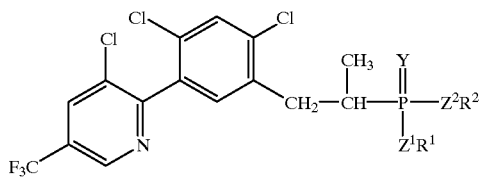

the compound Ieγ.1–Ieγ.429, which differ from the corresponding compounds Iaα.1–Iaα.429 only by the fact that X is —CH$_2$—CH(CH$_3$)— and R$^4$ is fluorine:

Ieγ

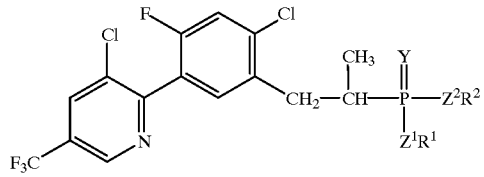

the compounds Ifα.1–Ifα.429, which differ from the corresponding compounds Iaα.1–Iaα.429 only by the fact that X is —CH$_2$—CH(CN)—:

Ifα

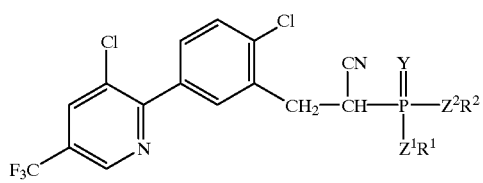

the compounds Ifβ.1–Ifβ.429, which differ from the corresponding compounds Iaα.1–Iaα.429 only by the fact that X is —CH$_2$—CH(CN)— and R$^4$ is chlorine:

Ifβ

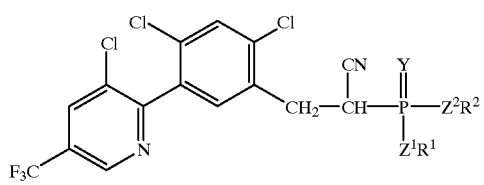

the compounds Ifγ.1–Ifγ.429, which differ from the corresponding compounds Iaα.1–Iaα.429 only by the fact that X is —CH$_2$CH(CN)— and R$^4$ is fluorine:

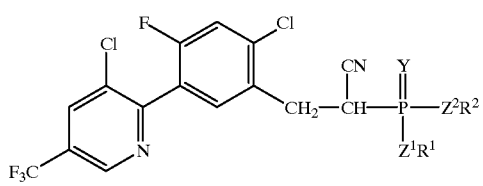
Ifγ

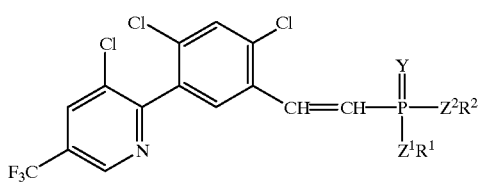
Ihβ the compounds Igα.1–Igα.429, which differ from the corresponding compounds Iaα.1–Iaα.429 only by the fact that X is —CH₂—CH(COOCH₃)—:

the compounds Ihγ.1–Ihγ.429, which differ from the corresponding compounds Iaα.1–Iaα.429 only by the fact that X is ethene-1,2-dyl and R⁴ is fluorine:

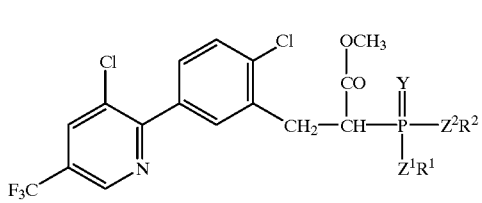
Igα

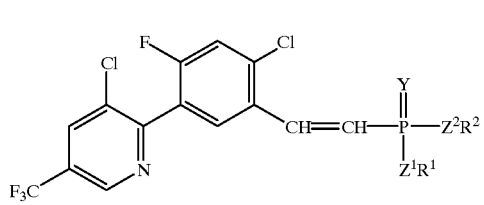
Ihγ the compounds Igβ.1–Igβ.429, which differ from the corresponding compounds Iaα.1–Iaα.429 only by the fact that X is —CH₂—CH(COOCH₃)— and R⁴ is chlorine:

the compounds Iiα.1–Iiα.429, which differ from the corresponding compounds Iaα.1–Iaα.429 only by the fact that X is —CH=C(Cl)—:

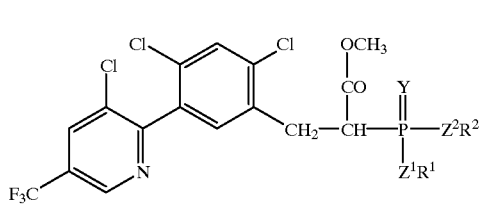
Igβ

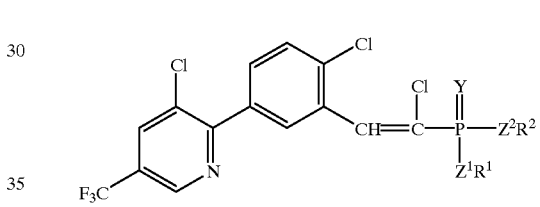
Iiα the compounds Igγ.1–Igγ.429, which differ from the corresponding compounds Iaα.1–Iaα.429 only by the fact that X is —CH₂—CH(COOCH₃)— and R⁴ is fluorine:

the compounds Iiβ.1–Iiβ.429, which differ from the corresponding compounds Iaα.1–Iaα.429 only by the fact that X is —CH=C(Cl)— and R⁴ is chlorine:

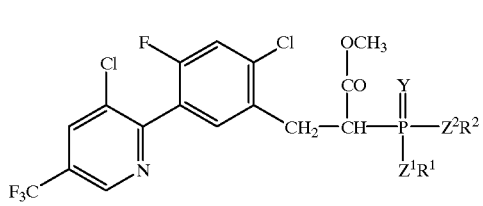
Igγ

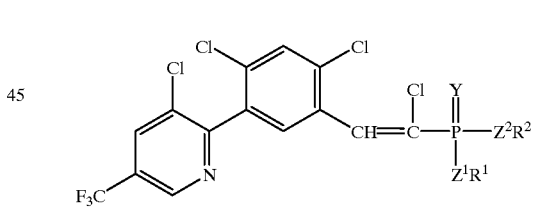
Iiβ the compounds Ihα.1–Ihα.429, which differ from the corresponding compounds Iaα.1–Iaα.429 only by the fact that X is ethene-1,2-diyl:

the compounds Iiγ.1–Iiγ.429, which differ from the corresponding compounds Iaα.1–Iaα.429 only by the fact that X is —CH=C(Cl)— and R⁴ is fluorine:

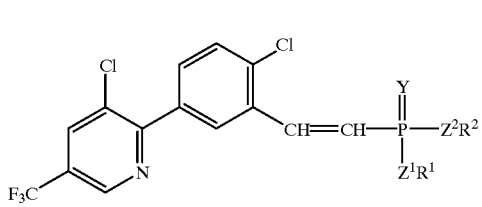
Ihα

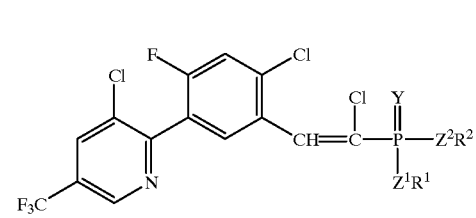
Iiγ the compounds Ihβ.1–Ihβ.429, which differ from the corresponding compounds Iaα.1–Iaα.429 only by the fact that X is ethene-1,2-dyl and R⁴ is chlorine:

the compounds Ijα.1–Ijα.429, which differ from the corresponding compounds Iaα.1–Iaα.429 only by the fact that X is —CH=C(Br)—:

Ijα

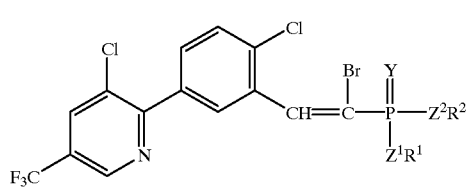

the compound Ijβ.1–Ijβ.429, which differ from the corresponding compounds Iaα. 1–Iaα.429 only by the fact that X is —CH=C(Br)— and R⁴ is chlorine:

Ijβ

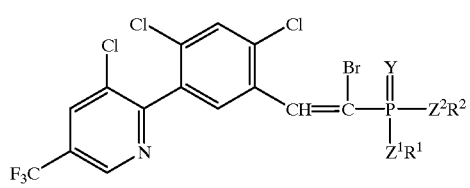

the compound Ijγ. 1–Ijγ.429, which differ from the corresponding compounds Iaα.1–Iaα.429 only by the fact that X is —CH=C(Br)— and R⁴ is fluorine:

Ijγ

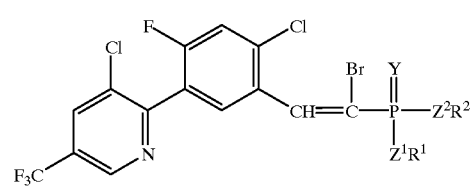

the compounds Ikα.1–Ikα.429, which differ from the corresponding compounds Iaα.1–Iaα.429 only by the fact that X is —CH=C(CH₃)—:

Ikα

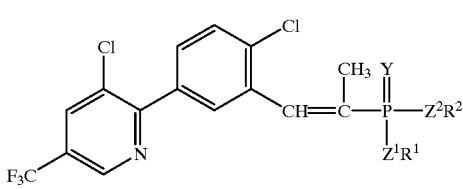

the compounds Ikβ.1–Ikβ.429, which differ from the corresponding compounds Iaα.1–Iaα. 429 only by the fact that X is —CH=C(CH₃)— and R⁴ is chlorine:

Ikβ

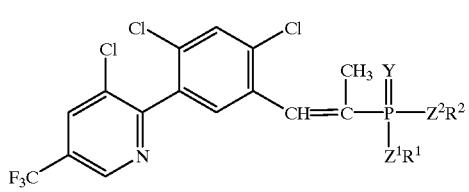

the compounds Ikγ.1–Ikγ. 429, which differ from the corresponding compounds Iaα.1–Iaα.429 only by the fact that X is —CH=C(CH₃)— and R⁴ is fluorine:

Ikγ

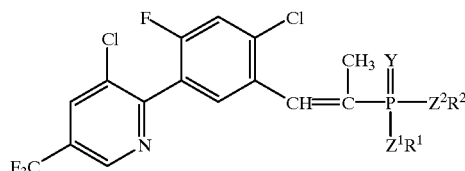

the compounds IIα.1–IIα.429, which differ from the corresponding compounds Iaα.1–Iaα.429 only by the fact that X is —CH=C(CN)—:

IIα

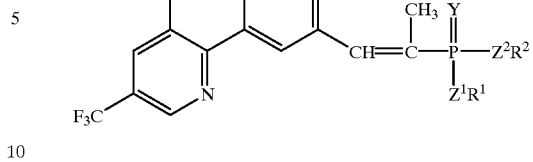

the compounds IIβ.1–IIβ.429, which differ from the corresponding compounds Iaα.1–Iaα. 429 only by the fact that X is —CH=C(CN)— and R⁴ is chlorine:

IIβ

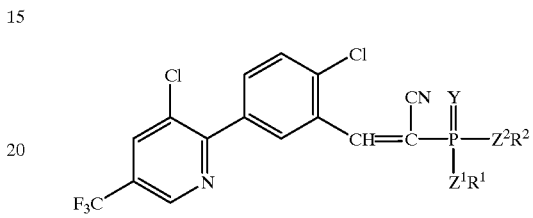

the compounds IIγ.1–IIγ.429, which differ from the corresponding compounds Iaα.1–Iaα.429 only by the fact that X is —CH=C(CN)— and R⁴ is fluorine:

IIγ

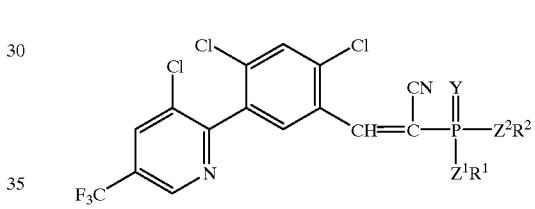

the compound Imα.1–Imα.429, which differ from the corresponding compounds Iaα.1–Iaα.429 only by the fact that X is —CH=C(COOCH₃)—:

Imα

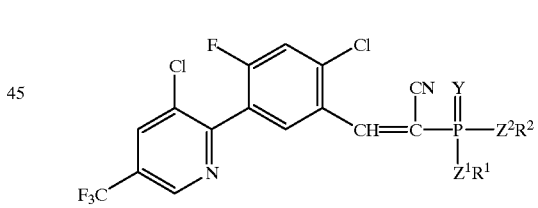

the compound Imβ.1–Imβ.429, which differ from the corresponding compounds Iaα.1–Iaα.429 only by the fact that X is —CH=C(COOCH₃)— and R⁴ is chlorine:

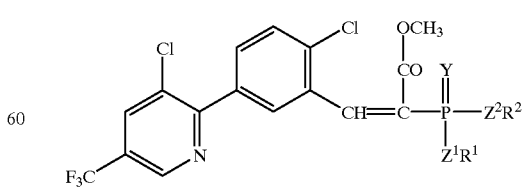

Imβ

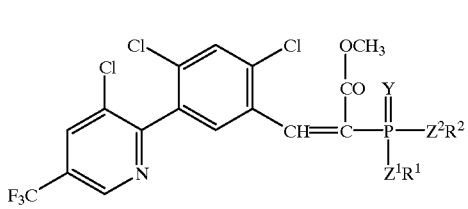

the compounds Imγ.1–Imγ.429, which differ from the corresponding compounds Iaα. 1–Iaα.429 only by the fact that X is —CH=C(C))CH$_3$)— and R$^4$ is fluorine:

Imγ

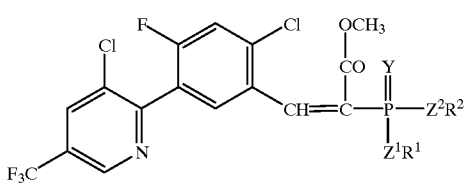

the compounds Inα.1–Inα.429, which differ from the corresponding compounds Iaα.1–Iaα.429 only by the fact that X is —CH—OCH$_2$—:

Inα

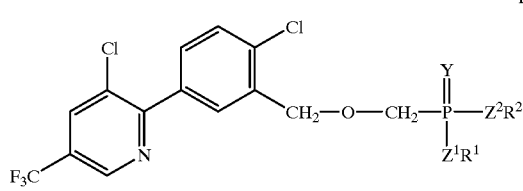

the compounds Inβ.1–Inβ.429, which differ from the corresponding compounds Iaα.1–Iaα.429 only by the fact that X is —CH—OCH$_2$— and R$^4$ is chlorine:

Inβ

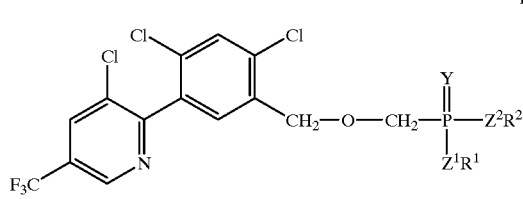

the compounds Inγ.1–Inγ.429, which differ from the corresponding compounds Iaα.1–Iaα.429 only by the fact that X is —CH—OCH$_2$— and R$^4$ is fluorine:

Inγ

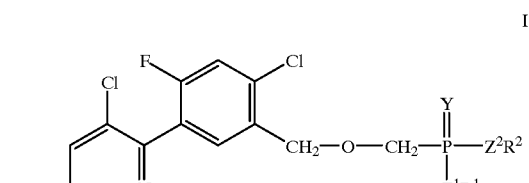

the compounds Ioα.1–Ioα.429, which differ from the corresponding compounds Iaα.1–Iaα.429 only by the fact that X is —OCH$_2$—:

Ioα

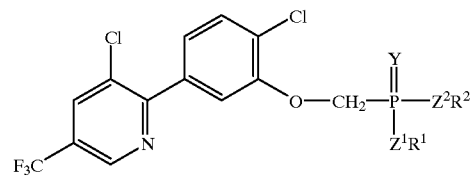

the compounds Ioβ.1–Ioβ.429, which differ from the corresponding compounds Iaα.1–Iaα.429 only by the fact that X is —OCH$_2$— and R$^4$ is chlorine:

Ioβ

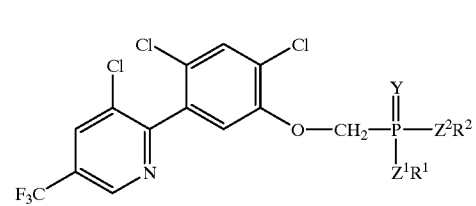

the compounds Ioγ.1–Ioγ. 429, which differ from the corresponding compounds Iaα.1–Iaα.429 only by the fact that X is —OCH$_2$— and R$^4$ is fluorine:

Ioγ

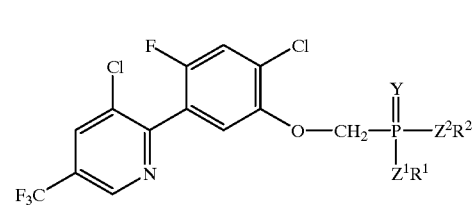

The substituted 2-phenylpyridines of the formula I are accessible in various ways, in particular by one of the following processes:

A) By linking the phosphonyl group with the phenylpyridine moiety

A.1) by diazotizing 3-pyridylanilines II and reacting the resulting diazonium salts with vinyl- or alkynylphosphonic acid derivatives III by the method of Meerwein {cf., for example, Org. Reactions 11, (1960), chapter 3, pp. 189–260 and Kogyo Kagaku Zasshi 67(12), (1964), 2093–2095}:

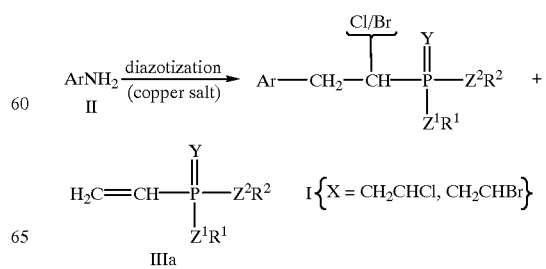

-continued

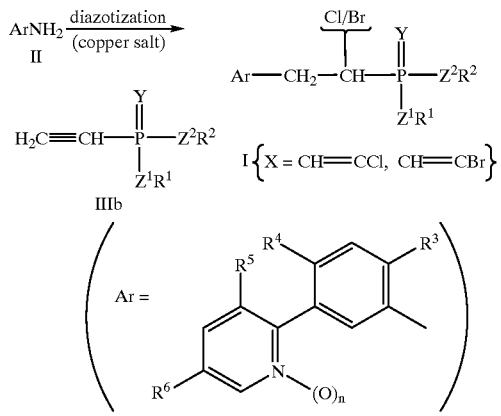

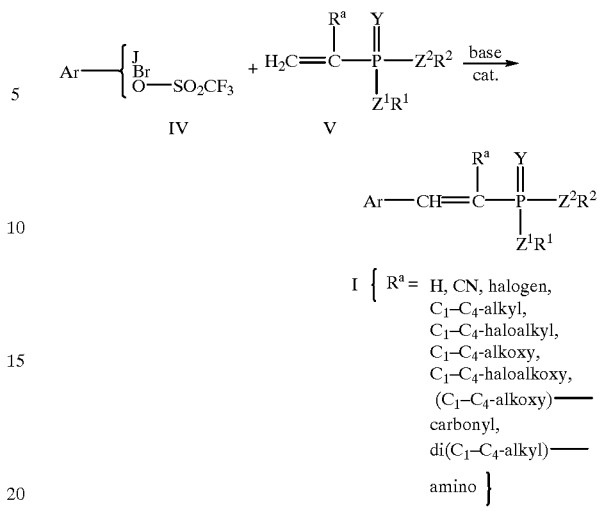

In this method, the 3-pyridylaniline of the formula II, which is either known from the literature or can be prepared similarly to anilines known from the literature, is first converted in a manner known per se to give the corresponding diazonium cation, and this is then reacted fully with IIIa or IIIb in the presence of a copper salt.

The diazonium salt is generally obtained by reacting the 3-pyridylaniline II with a nitrite such as sodium nitrite and potassium nitrite in an aqueous solution of an acid, e.g. in aqueous hydrofluoric acid, hydrochloric acid, hydrobromic acid, sulfuric acid or tetrafluoroboric acid. The nitrite is normally employed in approximately five times the molar amount based on the amount of 3-pyridylaniline II.

The resulting solution of the diazonium salt, or the diazonium salt isolated therefrom, is then reacted with a solution or suspension of the vinyl- or alkynylphosphonic acid derivative IIa/IIb in the presence of a copper salt such as copper(I) bromide, copper(II) bromide, copper(I) chloride and copper(II) chloride.

Examples of suitable solvents are water, acetonitrile, ketones such as acetone, diethyl ketone and methyl ethyl ketone, ethers such as diethyl ether and tetrahydrofuran, and furthermore alcohols such as methanol or ethanol.

Normally, the vinyl- or alkynylphosphonic acid derivatives IIIa/IIIb and the copper halide are used in approximately equimolar amounts or in an excess of up to approximately thirty times the molar amount, based on the 3-pyridylaniline II. However, the copper halide can also be employed in smaller or catalytic amounts.

In general, the diazotization and reaction of the diazonium salt the IIIa/IIIb are carried out at from (−100) to 50° C., preferably (−20) to +30° C.

One process variant consists in adding a nitrous ester such as tert-butyl nitrite and isopentyl nitrite, to a solution or suspension of the 3-pyridylaniline II, of the vinyl- or alkynylphosphonic acid derivative IIIa/IIIb and of the copper halide in an aqueous system, e.g. in glacial acetic acid/ hydrogen chloride, absolute methanol or ethanol, in an ether such as tetrahydrofuran and dioxane or in acetonitrile or acetone. What has been said above for the reaction temperature and the proportions of the reactions also applies here.

A.2) by a Heck reaction (see, for example, A. Burini, S. Cacchi, P. Pace, B. R. Pietroni, Synlett 1995, 677):

Regarding the definition of Ar, see process A.1); cat. is a transition metal catalyst, preferably a palladium (II) compound such as palladium acetate.

In general, the reaction is carried out in an inert organic solvent, in particular in dimethylformamide or tetrahydrofuran.

Examples of suitable bases are carbonates such as potassium carbonate, acetates such as sodium acetate and tertiary amines such as triethylamine.

The reaction is generally carried out at from 0° C. to the boiling point of the reaction mixture, preferably at 50 to 100° C.

A.3) by Knoevenagel condensation of aromatic aldehydes VIa or ketones VIb with phosphonic acid derivatives VII:

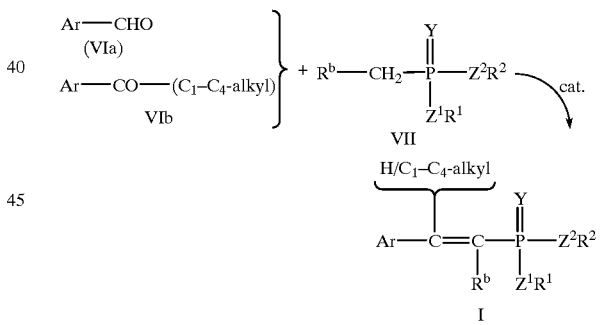

As regards the definition of Ar, see process A.1);

$R^b$ is cyano, $C_1$–$C_4$-alkoxy or ($C_1$–$C_4$-alkoxy)carbonyl;

cat. is a catalyst, e.g. piperidine/acetic acid, sodium methoxide, sodium ethoxide, titanium tetrachloride/N-methylmorpholine, or chlorotri (isopropoxy) titanium/ triethylamine.

The process is normally carried out in an inert organic solvent, e.g., in an aromatic hydrocarbon such as toluene, a lower alcohol such as methanol and ethanol or in a chlorinated hydrocarbon such as dichloromethane.

The reaction temperature is generally from 0° C. to the boiling point of the reaction mixture.

The water which is liberated during the reaction can be removed by means of azeotropic distillation, if so desired. In this case, the process is preferably carried out in an aromatic hydrocarbon such as benzene, toluene and the xylenes at the particular boiling point of the reaction mixture {see, for example, S. Abdallah-El Ayoubi, F. Texier-Boullet, J. Hamelin, Synthesis 1994, 258; D. Danion, R. Carrie, Tetrahedron Lett. 1968, 4537; F. Texier-Boullet, A. Foucaud, Tetrahedron Lett. 21 (1980) 2161; S. Patai, A. Schwartz, J. Org. Chem. 25 (1960), 1232; J. M. McIntosh, R. A. Sieler, Can. J. Chem. 56 (1978) 226; M. T. Reetz, R. Peter, M. v. Itzstein, Chem. Ber. 120 (1987) 121; K. A. Petrov, V. A. Chauzov, S. V. Agafonov, N. V. Pazhitnova, J. Gen. Chem. USSR 50 (1980) 1225}.

Those aromatic aldehydes VIa or ketones VIb which are not already known can be prepared in a manner known per se.

A.4) by Wittig-Horner olefination {cf., for example, B. M. G. T. Lowen, M. R. Almond, J. Org. Chem 59 (1994) 4548; P. Teulade, P. Savignac, E. E. Aboujaoude, S. Liétge, N. Collignon, J. Organomet. Chem. 304 (1986) 283; G. M. Parratt, J. Chem. Soc., Perkin Trans. 1 (1986), 1417; B. Costisella, I. Keitel H. Gross, Tetrahedron 37 (1981) 1227}:

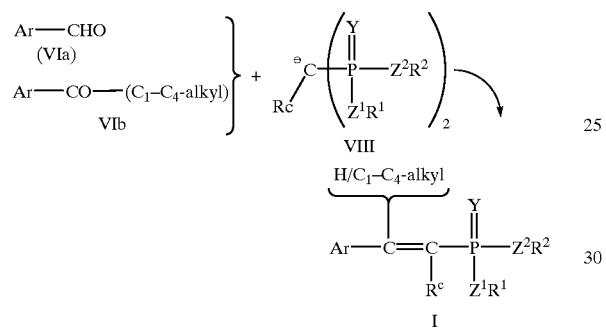

As regards the definition of Ar, see process A.1);

$R^c$ is hydrogen, halogen, $C_1$–$C_4$-alkyl or di($C_1$–$C_4$-alkyl)amino.

The process is normally carried out in an inert organic solvent, e.g. in an aromatic hydrocarbon such as toluene, a halogenated hydrocarbon such as dichloromethane or an ether such as diethyl ether, tetrahydrofuran, dioxane and 1,2-dimethoxyethene.

The anion VIII can be obtained, for example, by deprotonating the corresponding methanediphorphonic acid derivative with a strong base such as lithium diisopropylamide, sodium hydride and n-butyllithium.

The reaction is generally carried out at from (–100)°C. to the boiling point of the reaction mixture, preferably at (–78) to +30° C.

A.5) by Wittig olefination {see, in this context, for example GB-A 12 43 214}:

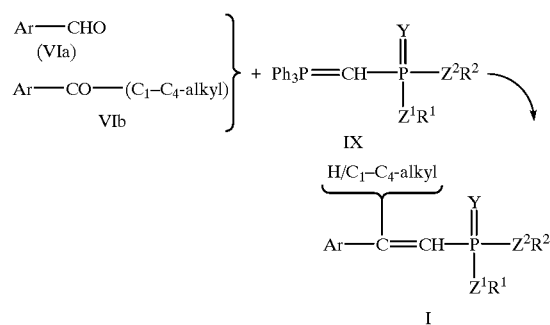

As regards the definition of Ar, see process A.1);

Ph is the phenyl group.

The process is normally carried out in an inert organic solvent, e.g. in an aromatic hydrocarbon such as toluene, a halogenated hydrocarbon such as dichloromethane or an ether such as diethyl ether, tetrahydrofuran, dioxane and 1,2-di-methoxyethane.

The reaction is generally carried out at from (–100)°C. to the boiling point of the reaction mixture, preferably at 20 to 60° C.

A.6) by Peterson olefination {see, in this context, for example O. I. Kolodyazhnyi, D. B. Golokhov, J. Gen. Chem. USSR 57 (1987) 2353; F. A. Carey, A. S. Court, J. Org. Chem. 37 (1972) 939}:

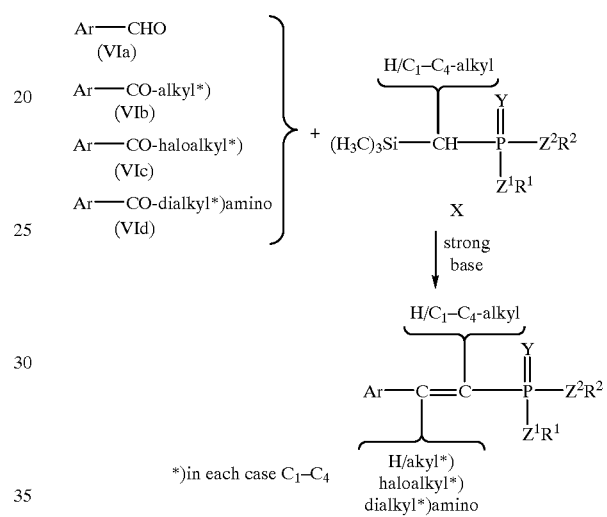

The reaction is normally carried out in an inert organic solvent, e.g. in an aromatic hydrocarbon such as toluene or an ether such as diethyl ether, tetrahydrofuran, dioxane and 1,2-dimethoxyethane.

Examples of suitable strong bases are lithium diisopropylamide, sodium hydride or butyllithium.

The reaction is generally carried out at from (–100)°C. to the boiling point of the reaction mixture, preferably at (–70) to +30° C.

Those aromatic aldehydes VIa, ketones VIb and VIc and the N,N-dialkylbenzamides VId which are not already known can be prepared in a manner known per se.

A.7) by coupling a styryl halide XI with a trialkyl phosphite XII or a dialkyl phosphite XIII {cf. in this context, for example, R. S. Gross, S. Mehdi, J. R. McCarthy, Tetrahedron Lett. 34 (1993) 7197; G. Axelrad, S. Laosooksathit, R. Engel, J. Org. Chem. 46 (1981) 5200}:

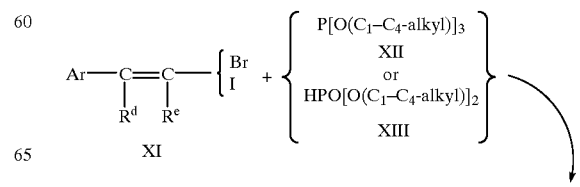

-continued

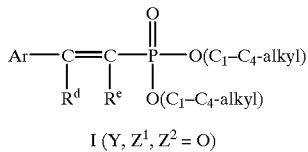

I (Y, Z$^1$, Z$^2$ = O)

As regards the definition of Ar, see process A.1);

R$^d$,R$^e$ are hydrogen, halogen or C$_1$–C$_4$-alkyl.

The process is normally carried out in an inert organic solvent, preferably in an aromatic hydrocarbon such as toluene or an ether such as tetrahydrofuran.

The reaction of XI with a trialkyl phosphite XII is advantageously carried out in the presence of copper(I) bromide or copper(I) chloride.

The reaction of XI with a dialkyl phosphite XIII is advantageously carried out in the presence of a transition metal catalyst, preferably a palladium(II) compound such as dichlorobis(triphenylphosphine)palladium, and, if desired, in the presence of a base, e.g. triethylamine.

The reaction is generally carried out at from (–100)°C. to the boiling point of the reaction mixture, preferably at approximately +25° C.

Those styryl halides XI and those phosphorus compounds XII and XIII which are not already known can be prepared in a manner known per se.

A.8) by reacting a phenylacetylene XIV
  with a trialkyl phosphite XII or
  in succession with phosphorus pentachloride and an alcohol, mercaptan or amine (HZ$^1$R$^1$/HZ$^2$R$^2$) in the presence of a base
{cf., in this context, for example C. E. Griffin, T. D. Mitchell, J. Org. Chem. 30 (1965) 1935; A. Meisters, J. M. Swan, Aust. J. Chem. 18 (1965) 155; L. Maier, Synth. Inorg. Met. Org. Chem. 3 (1973) 329; A. A. Petrov, J. Gen. Chem. USSR 41 (1971) 1670}:

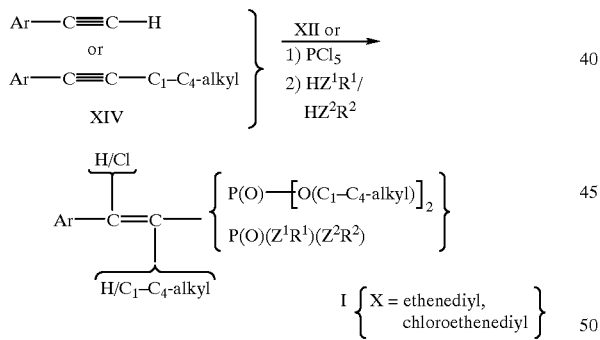

I { X = ethenediyl, chloroethenediyl }

As regards the definition of Ar, see process A.1).

The reaction of XIV with XII is preferably carried out in the absence of a solvent at from 20° C. to the boiling point of the trialkyl phosphite XII, in particular at the boiling point of the reaction mixture.

Bases which are suitable in the reaction of the phenylacetylene XIV with PCl$_5$ and (HZ$^1$R$^1$/HZ$^2$H$^2$) are, in particular, tertiary amines such as pyridine and triethylamine.

The reaction of XIV with PCl$_5$ is preferably carried out at from 50 to 200° C., the subsequent reaction with (HZ$^1$R$^1$/HZ$^2$R$^2$), in contrast, at from (–100)°C. to the boiling point of the reaction mixture.

Those phenylacetylenes XIV and alcohols, mercaptans and amines (HZ$^1$R$^1$/HZ$^2$R$^2$) which are not already known can be prepared in a manner known per se.

A.9) by reacting benzylidenetriphenylphosphoranes XV with a perfluoroalkanecarboxylic anhydride and subsequently with a lithium dialkyl phosphite in a manner known per se {cf. in this context, for example, Y. Shen, Q. Liao, W. Qiu, J. Chem. Soc., Perkin Trans 1, 695 (1990)}:

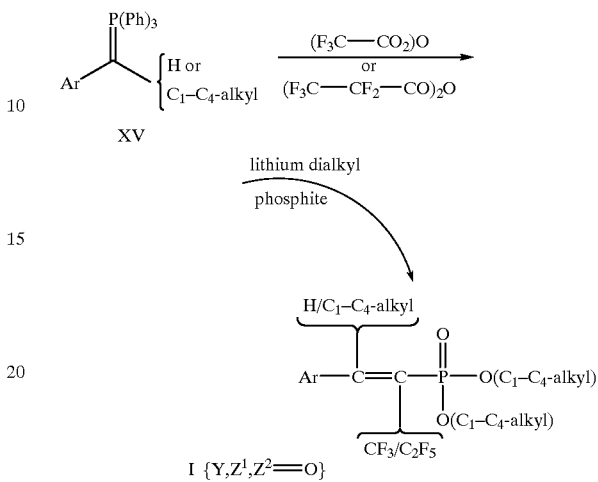

I {Y,Z$^1$,Z$^2$=O}

As regards the definition of Ar, see process A.1);

Ph is the phenyl group.

Those benzylidenetriphenylphosphoranes XV which are not already known can be prepared in a manner known per se.

A.10) by alkylating a phosphonic acid derivative XVI in a manner known per se using a 3-pyridylbenzyl halide XVII in the presence of a strong base {cf. in this context, for example, G. M. Blackburn, M. J. Parratt, J. Chem. Soc., Perkin Trans 1, 1425 (1986); G. M. Kosolapoff, J. S. Powell, J. Am. Chem. Soc. 72 (1950) 4198; R. M. Keenan et al., J. Med. Chem. 35 (1992) 3858; H. Ahlbrecht, W. Farnung, Synthesis, 336 (1977); E. D'Incan, J. Seyden-Penne, Synthesis, 516 (1975); S. Hanessian, Y. L. Bennani, D. Delorme, Tetrahedron Lett. 31 (1990) 6461}:

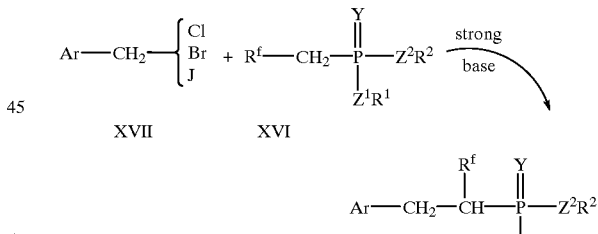

I{X = ethanediyl; or ethanediyl
  which is substituted by
  cyano, halogen, C$_1$–C$_4$-alkyl,
  (C$_1$–C$_4$-alkoxy)carbonyl or
  di(C$_1$–C$_4$-alkyl)amino}

As regards the definition of Ar, see process A.1);

R$^f$ is hydrogen, cyano, halogen, C$_1$–C$_4$-alkyl, (C$_1$–C$_4$-alkoxy)carbonyl or di(C$_1$–C$_4$-alkyl)amino.

Examples of suitable strong bases are sodium hydroxide, butyllithium and lithium diisopropylamide.

The process is normally carried out in an inert organic solvent, preferably in an aromatic hydrocarbon such as toluene or a cyclic ether such as tetrahydrofuran.

In general, the process is carried out at from (–100)°C. to the boiling point of the reaction mixture, preferably from (–78)°C. to +25° C.

Those phosphonic acid derivatives XVI and those benzyl halides XVII which are not already known can be prepared in a manner known per se.

A.11) by reacting aldehydes XVIIIa/XVIIIb with dialkyl phosphites XIII, if desired in the presence of ammonia or a primary or secondary amine {cf. in this context, for example, M. E. Chalmers, G. M. Kosolapoff, J. Am. Chem. Soc. 75 (1953) 5278; C. Li, C. Yuan, Tetrahedron Lett. 34 (1993) 1515}:

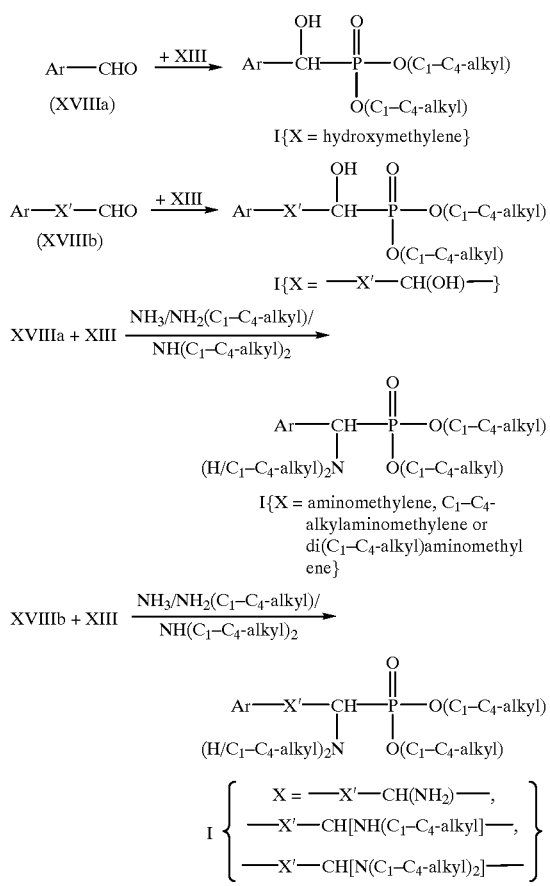

As regards the definition of Ar, see process A.1);

X' is unsubstituted or substituted —$CH_2$—, —$CH_2CH_2$—, —$OCH_2$— or —$SCH_2$—, substituents which are possible being the same as in the corresponding meanings of X.

Examples of suitable solvents are water, the lower alcohols such as methanol, ethers such as tetrahydrofuran and diethyl ether, and also pyridine.

In general, the process is carried out at from (−100)°C. to the boiling point of the reaction mixture, preferably from 20 to 50° C.

Those aldehydes XVIIIa/XVIIIb which are not already known can be prepared in a manner known per se.

A.12) by reacting alkyl halides XVII or XIX with trialkyl phosphites XII in a manner known per se by the method of Arbuzov {see in this context, for example, A. Y. Garner, E. C. Chapin, P. M. Scanlon, J. Org. Chem. 24 (1959) 532; A. G. Schultz, J. J. Napier, R. Ravichandran, J. Org. Chem. 48 (1983) 3408; Y. Vo-Quang, D. Carniato, L. Vo-Quang, F. Le Goffic, J. Chem. Soc., Chem. Commun., 1505 (1983)}:

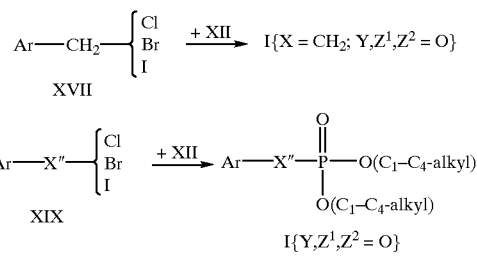

As regards the definition of Ar, see process A.1);

X" is, in this context, —$OCH_2$—, —$SCH_2$— or —Q—$CH_2$— where Q=unsubstituted or substituted methylene, 1,2-ethanediyl, oxymethylene, thiamethylene, methyleneoxy or methylenethia.

The reaction is preferably carried out in the absence of a solvent, at from 0° C. to the boiling point of the trialkyl phosphite XII, preferably from 20 to 150° C.

Those alkyl halides XIX which are not already known can be prepared in a manner known per se.

A.13) by nucleophilic substitution reaction on phosphonic acid derivatives XXI in the presence of a base {cf. in this context, for example, J. L. Kelley, J. A. Linn, E. W. McLean, J. V. Tuttle, J. Med. Chem. 36 (1993) 3455}:

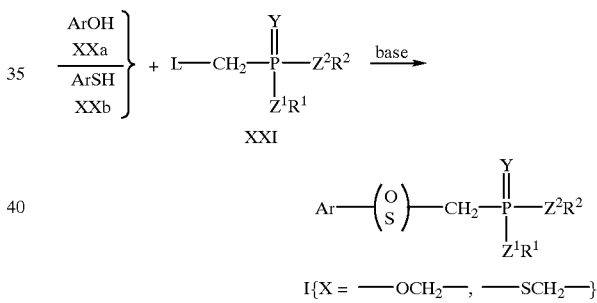

As regards the definition of Ar, see process A.1);

L is halogen or a customary leaving group such as methylsulfonyloxy or 4-tolylsulfonyloxy.

The process is normally carried out in an inert organic solvent, preferably in pyridine, a ketone such as acetone, or in an ether such as tetrahydrofuran.

Examples of suitable bases are butyllithium and alkali metal hydrides such as sodium hydride or alkali metal carbonates such as potassium carbonate.

In general, the process is carried out at from (−100)°C. to the boiling point of the reaction mixture, preferably from 20 to 50° C.

A further possibility of synthesizing compounds I by means of a nucleophilic substitution reaction is to react 3-pyridylbenzyl halides XVII with phosphonic acid derivatives XXII in a manner known per se in the presence of a base {see in this context, in addition to the abovementioned references, also S. Jarosz, E. Koslowska, Z. Ciunik, Pol. J. Chem. 68 (1994) 2209}:

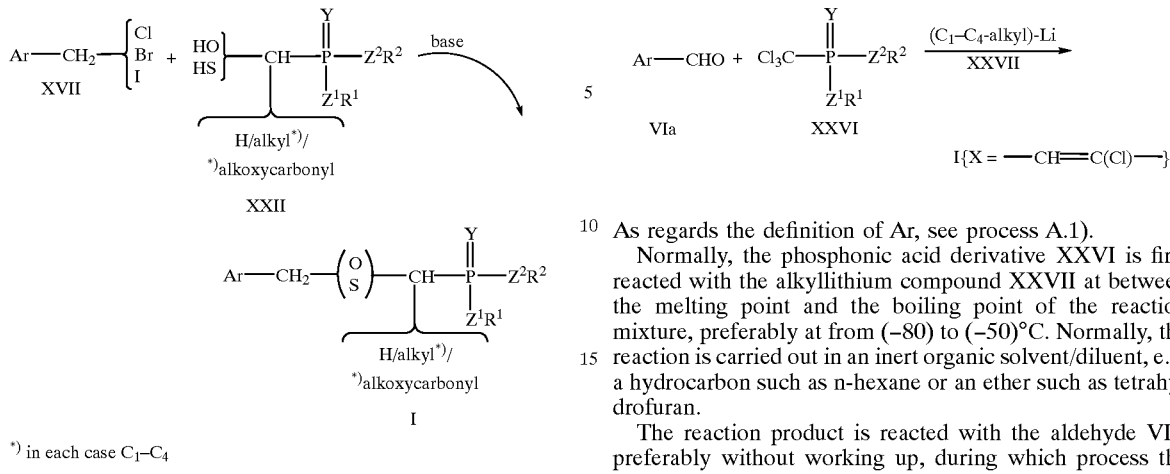

*) in each case $C_1$–$C_4$

As regards Ar, solvent, base and reaction temperature, reference may be made to the above information on the reaction of XX with XXI.

Those phenols XXa and thiophenols XXb, those phosphonic acid derivatives XXI, those benzyl halides XVII and those phosphonic acid derivatives XXII which are not already known can be prepared in a manner known per se.

A.14) by reacting a phenol XXa with a halomethyl thioether XXIII in the presence of a base, halogenolytic cleavage of the resulting alkyl thioalkyl ether XXIV, followed by an Arbuzov reaction:

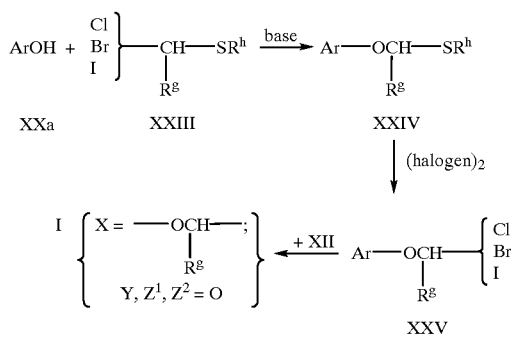

As regards the definition of Ar, see process A.1);

$R^g$, $R^h$ independently of one another are $C_1$–$C_4$-alkyl radicals (XXIIIa=XXIII where $R^g$=H and $R^h$=$CH_3$; XXIVa=XXIV where $R^g$=H und $R^h$=$CH_3$).

As regards the procedure of the nucleophilic substitution reaction XXA+XXIII, reference may be made to the information given in Section A.13).

The subsequent cleavage of the reaction product XXIV is carried out with a halogen, preferably with chlorine or bromine, at between the melting point and the boiling point of the reaction mixture, preferably at 0–100° C. As a rule, the reaction is carried out in an inert organic solvent, e.g. a hydrocarbon such as n-hexane, a halogenated hydrocarbon such as dichloromethane or an ether such as tetrahydrofuran.

Finally, the halomethyl ether XXV is subjected to an Arbuzov reaction with a trialkyl phosphite XII. As regards the procedure of this reaction, reference may be made to the information given in Section A.12).

A.15) by reacting an aldehyde VIa with a trichloromethanephosphonic acid derivative XXVI in the presence of an alkyllithium compound XXVII:

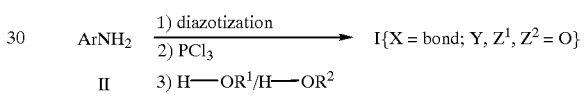

$I\{X = $—$CH$=$C(Cl)$—$\}$

As regards the definition of Ar, see process A.1).

Normally, the phosphonic acid derivative XXVI is first reacted with the alkyllithium compound XXVII at between the melting point and the boiling point of the reaction mixture, preferably at from (−80) to (−50)°C. Normally, the reaction is carried out in an inert organic solvent/diluent, e.g. a hydrocarbon such as n-hexane or an ether such as tetrahydrofuran.

The reaction product is reacted with the aldehyde VIa, preferably without working up, during which process the reaction temperature is preferably raised to approximately 20° C.

A.16) by diazotizating of pyridylanilines II, reacting the resulting diazonium salts with phosphous trichloride and reacting the reaction products with nucleophiles H—$OR^1$ or H—$OR^2$ {see, for example, E. Klumpp, G. Eifert, P. Born, J. Szulagyi, Chem. Ber. 122, (1989), 2021; G. O. Doak et al., J. Am. Chem. Soc. 75, (1953), p. 683, 1379, 4903 and 4905}:

$$ArNH_2 \xrightarrow[\text{2) PCl}_3]{\text{1) diazotization}} I\{X = \text{bond}; Y, Z^1, Z^2 = O\}$$

II    3) H—$OR^1$/H—$OR^2$

As regards the diazotization, reference may be made to the information given in section A.1).

The diazonium salt is preferably isolated prior to the reaction using phosphorus trichloride, for example as the halide, tetrafluoroborate or hexafluorophosphate. The reaction itself is generally carried out in an inert organic solvent, e.g. a hydrocarbon such as n-hexane and toluene, a halogenated hydrocarbon such as dichloromethane, an ether such as tetrahydrofuran, or an aprotic solvent such as acetonitrile, dimethylformamide and dimethyl sulfoxide.

In general, the process is carried out between the melting point and the boiling point of the reaction mixture, preferably at from 0 to 100° C.

The subsequent conversion into I is preferably carried out using water as the nucleophile.

A.17) by reacting an aryl halide/triflate of the formula IV with a dialkyl phosphite XIII in the presence of a base and of a transition metal catalyst {see, for example, A. Castelnuovo, J. Calabrese, J. Am. Chem. Soc. 112 (1990), 4324; T. Hirao et al., Bull. Chem. Soc. Jpn. 55 (1982), 909}:

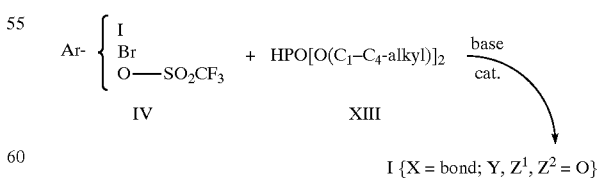

$I \{X = \text{bond}; Y, Z^1, Z^2 = O\}$

Examples of suitable bases are amines such as triethylamine.

A suitable catalyst is preferably a palladium compound, for example tetrakis(triphenylphosphine)palladium. Apart from this, reference may be made to the information given in section A.2).

B) Derivatization of substituted 2-phenylpyridines of the formula I:

B.1) Hydrogenation of substituted 2-phenylpyridines I where X is 1,2-ethenediyl or a halogen-substituted B.2) Hydrolysis of substituted 2-phenylpyridines I, conversion of the process products into phosphonyl halides, and reaction of the latter with nucleophiles:

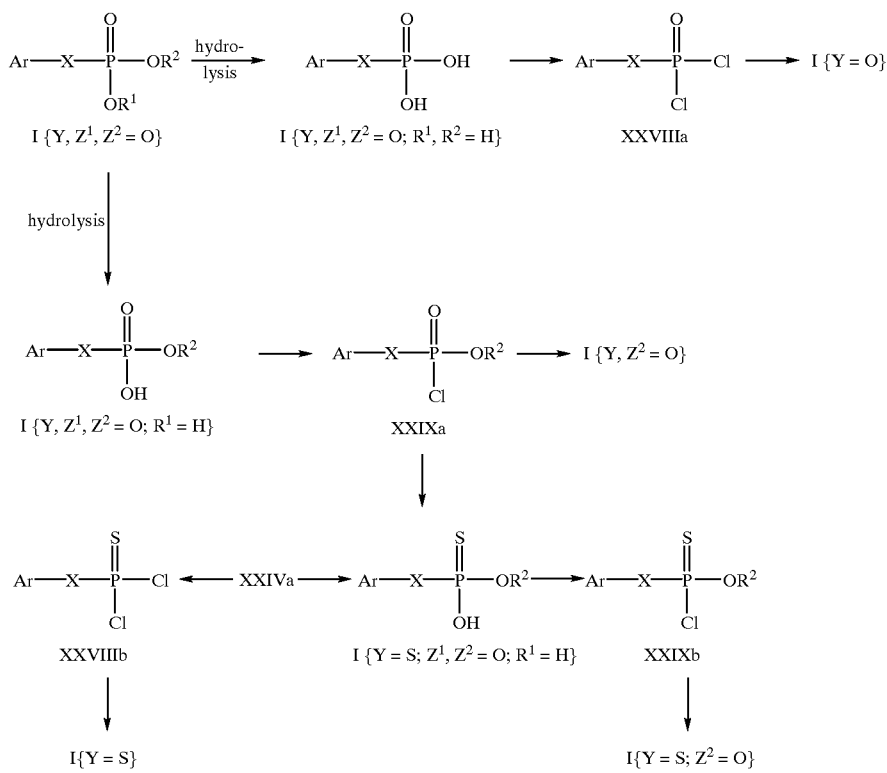

methylene, 1,2-ethanediyl or 1,3-propanediyl bridge {cf., for example, C. N. Robinson, P. K. Li. J. F. Addison, J. Org. Chem. 37 (1972) 2939; G. T. Lowen, M. R. Almond, J. Org. Chem. 59 (1994) 4548}:

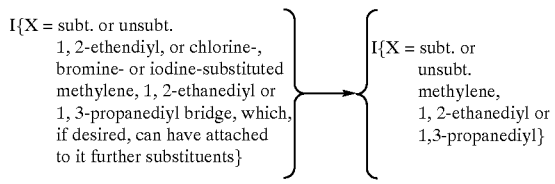

As regards the definition of Ar, see process A.1).

The hydrogenation is carried out either with hydrogen in the presence of a catalyst conventionally used for this purpose, such as palladium or platinum on active charcoal or Raney nickel, at from 0 to 150° C. and a hydrogen pressure of approx. 1 to 200 bar, or with a metal hydride such as sodium borohydride and lithium aluminum hydride at from 0° C. to the boiling point of the reaction mixture.

Examples of solvents which are suitable for the hydrogenation with hydrogen are water, the lower alcohols such as methanol and ethanol, ethers such as diethyl ether and tetrahydrofuran or esters such as ethyl acetate.

When reacting the starting compound with a metal hydride, the process is preferably carried out in an inert organic solvent, in particular an ether such as diethyl ether and tetrahydrofuran.

As regards the definition of Ar, see process A.1).

In this process, the substituted 2-phenylpyridines I are first cleaved hydrolytically (acidic or alkaline) or, if $R^1$ and/or $R^2$ is a benzyl or allyl radical, also hydrogenolytically, to give phosphonic acids and phosphonic monesters I. If desired, the cleavage can also be carried out by means of a reaction with a tri($C_1$–$C_4$-alkyl)silyl halide such as chlorotrimethylsilane, iodotrimethylsilane or a mixture of chlorotrimethylsilane and alkali metal iodine.

The cleavage products can then be converted into the corresponding phosphonyl monochlorides or phosphonyl dichlorides XXVIIIa and XXIXa by reaction with a halogenating agent such as oxalyl chloride, thionyl chloride and phosphorus pentachloride.

If desired, the phosphonyl dichlorides XXVIIIa can be thionated in a manner known per se using a thionating agent such as phosphorus(V) sulfide and 2,4-bis(4-methoxyphenyl)-1,3,2,4-dithiadiphosphetane-2,4-dithione ("Lawesson Reagent") to give thionophosphonyl dichlorides XXVIIIb. As regards useful solvents, temperature and ratios, reference may be made to the information given in DE-A 19 504 188 under process D).

Finally, further substituted 2-phenylpyridines I are accessible by reacting XXVIII and XXIX with nucleophiles $HZ^1R^1$ or $HZ^2R^2$.

The chlorophosphonates XXIXa can be converted into the thionophosphonic monoesters XXIXb for example by conversion with sodium hydrogen sulfide.

As regards the procedure of the reaction and the ratios of the reactants, reference may be made, for example, to Houben-Weyl, Methoden der Organischen Chemie [Methods in Organic Chemistry], Georg Thieme Verlag, Stuttgart, Vol. 12/1, 4th, Edition 1963, pp. 387 et seq., 407 et seq. and 557 et seq.; Vol. E2 1982, pp. 300 et seq. and 419 et seq.

B.3) Elimination of hydrogen halide from compounds I where X=—CH$_2$—CH(halogen)— or —CH=C(halogen)—:

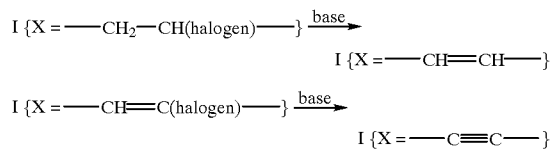

The process is normally carried out in water or in an inert organic solvent, e.g. an alcohol such as ethanol, an ether such as diethyl ether, tetrahydrofuran and dioxane, or an aprotic solvent such as acetonitrile, dimethylformamide and dimethyl sulfoxide.

Examples of suitable bases are alkali metal hydroxides, alkali metal carbonates, alkali metal hydrides, alkyl-lithium compounds such as butyllithium, or organic amines such as triethylamine, 1,4-diazabicyclo[2.2.2.]octane (DABCO) and 1,8-diazabicyclo[5.4.0.]undec-7-ene (DBU).

In general, the reaction is carried out at from (−100)°C. to the boiling point of the reaction mixture, preferably at from 20° to 100° C.

C) Oxidation of substituted phenylpyridines of the formula I where n is zero and the substituent —X—P(=Y)(Z$^1$R$^1$)(Z$^2$R$^2$) does not contain sulfur, in a manner known per se {cf., for example, A. Albini & S. Pietra, heterocyclic N-oxides, CRC-Press Inc., Boco Raton, USA 1991; H. S. Mosher et al., Org. Synth. Coll. Vol. IV 1963, page 828; E. C. Taylor et al., Org. Synth. Coll. Vol. IV 1963, page 704; T. W. Bell et al., Org. Synth. 69 (1990), page 226}:

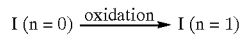

Amongst the oxidants conventionally used for oxidizing the pyridine ring, reference may be made way of example to peracetic acid, trifluoroperacetic acid, perbenzoic acid, m-chloroperbenzoic acid, monopermaleic acid, magnesium monoperphthalate, sodium perborate, Oxone® (contains peroxydisulfate), pertungstic acid and hydrogen peroxide.

Examples of suitable solvents are water, sulfuric acid, carboxylic acids such as acetic acid and trifluoroacetic acid, and halogenated hydrocarbons such as dichloromethane and chloroform.

Normally, the reaction mixture is successfully oxidized at from 0° C. to boiling point.

The oxidant is normally employed in at least equimolar amounts based on the starting compound. In general, an excess of oxidant has proved to be especially advantageous.

Unless otherwise specified, all processes described hereinabove are expediently carried out under atmospheric pressure or under the inherent pressure of the reaction mixture in question. The reactants are generally employed in a molar ratio of from 0.95:1 to 5:1.

In general, the reaction mixtures are worked up by methods known per se, for example by diluting the reaction solution with water followed by isolation of the product by means of filtration, crystallization or solvent extraction, or by removing the solvent, partitioning the residue in a mixture of water and a suitable organic solvent and working up the organic phase to give the product.

The substituted 2-phenylpyridines I can be obtained upon preparation in the form of isomer mixtures which, however, if desired, can be separated into the pure isomers by the methods conventionally used for such cases, such as crystallization or chromatography, also on an optically active absorbate. Pure optically active isomers can be prepared advantageously from suitably optically active starting materials.

Agriculturally useful salts of the compounds I can be formed by reaction with a base of the corresponding cation, preferably an alkali metal hydroxide or alkali metal hydride, or by reaction with an acid of the corresponding anion, preferably of hydrochloric acid, hydrobromic acid, sulfuric acid, phosphoric acid or nitric acid.

Salts of I whose metal ion is not an alkali metal ion can also be prepared in the customary manner by double decomposition of the corresponding alkali metal salt, also ammonium, phosphonium, sulfonium and sulfoxonium salts by means of ammonia, phosphonium hydroxide, sulfonium hydroxide or sulfoxonium hydroxide.

The compounds I and their agriculturally useful salts are suitable as herbicides, both in the form of isomer mixtures and in the form of the pure isomers. The herbicidal compositions comprising I effect very good control of vegetation on non-crop areas, especially at high rates of application. In crops such as wheat, rice, maize, soybeans and cotton they act against broadleaved weeds and grass weeds without damaging the crop plants substantially. This effect is observed especially at low rates of application.

Depending on the application method in question, the compounds I, or herbicidal compositions comprising them, can additionally be employed in a further number of crop plants for eliminating undersirable plants. Examples of suitable crops are the following: *Allium cepa, Ananas comosus, Arachis hypogaea, Asparagus officinalis, Beta vulgaris spec. altissima, Beta vulgaris spec. rapa, Brassica napus var. napus, Brassica napus var napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N. rustica), Olea europaea, Oryza sativa, Phaseolus, lunatus, Phaseolus vulgaris, Picea abies, Pinus spec., Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera* and *Zea mays*.

Moreover, the compounds I can also be used in crops which tolerate the action of herbicides due to breeding including genetic engineering methods.

Furthermore, the substituted 2-phenylpyridines I are also suitable for the desiccation and/or defoliation of plants.

As desiccants, they are especially suitable for desiccating the aerial parts of crop plants such as potatoes, oilseed rape, sunflowers and soybeans. This allows completely mechanical harvesting of these important crop plants.

Also of economic interest is facilitated harvesting, which is made possible by concentrating, over a period of time, dehiscence, or reduced adhesion to the tree, in the case of citrus fruit, olives or other species and varieties of pomaceous fruit, stone fruit and nuts. The same mechanism, i.e. promotion of the formation of abscission tissue between fruit or leaf and shoot of the plants is also essential for readily controllable defoliation of useful plants, in particular cotton.

Moreover, a shortened period of time within which the individual cotton plants ripen results in an increased fiber quality after harvesting.

The compounds I, or the compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring. The use forms depend on the intended purposes; in any case, they should guarantee the finest possible distribution of the active ingredients according to the invention.

Suitable inert auxiliaries are essentially: mineral oil fractions of medium to high boiling point such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidione and water.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants are the alkali metal, alkaline earth metal and ammonium salts of aromatic sulfonic acids, e.g. ligno-, phenol-, naphthalene- and dibutylnaphthalene-sulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite with liquors or methylcellulose.

Powders, materials for spreading and dusts can be prepared by mixing or concomitantly grinding the active substances with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the active ingredients I in the ready-to-use products can be varied within wide ranges. In general, the formulations comprise approximately from 0.001 to 98% by weight, preferably 0.01 to 95% by weight, of at least one active ingredient. The active ingredients are employed in a purity of from 90% to 100%, preferably 95% to 100% (according to NMR spectrum).

The formulation examples below illustrate the preparation of such products:

I. 20 parts by weight of the compound No. I$\alpha$.3 are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it wherein gives an aqueous dispersion which comprises 0.02% by weight of the active ingredient.

II. 20 parts by weight of the compound No. Ic$\alpha$.3 are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III. 20 parts by weight of the active ingredients No. Id$\alpha$.2 are dissolved in a mixture composed of 25 parts by weight of cyclohexanone, 65 parts by weight of a mineral oil fraction of boiling point 210° to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. If$\alpha$.3 are mixed thoroughly with 3 parts by weight of sodium diisobutylnaphthalene-$\alpha$-sulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the active ingredient No. I$\gamma$.2 are mixed with 97 parts by weight of finely divided kaolin. This gives a dust which comprises 3% by weight of the active ingredient.

VI. 20 parts by weight of the active ingredient No. I$\gamma$.3 are mixed intimately with 2 parts by weight of calcium dodecylbenzenesulfonate, 8 parts by eight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. In$\alpha$.3 is dissolved in a mixture composed of 70 parts by weight of cyclohexanone, 20 parts by weight of ethoxylated isooctylphenol and 10 parts by weight of ethoxylated castor oil. The mixture can subsequently be diluted with water to give the desired concentration of active ingredient. This gives a stable emulsion concentrate.

VIII. 1 part by weight of the compound No. IIα.38 is dissolved in a mixture composed of 80 parts by weight of cyclohexanone and 20 parts by weight of Wettol® EM 31 (=non-ionic emulsifier based on ethoxylated castor oil). The mixture can subsequently be diluted with water to give the desired concentration of active ingredient. This gives a stable emulsion concentrate.

The active ingredients I, or the herbicidal compositions comprising them, can be applied pre- or post-emergence. If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of undesirable plants which grow underneath, or the bare soil (post-directed, lay-by).

Depending on the intended aim of the control measures, the season, the target plants and the growth stage, the application rates of active ingredient I are from 0.001 to 3.0, preferably 0.01 to 1.0 kg/ha active substance (a.s.).

To widen the spectrum of action and to achieve synergistic effects, the substituted 2-phenylpyridines I can be mixed and applied jointly with a large number of representatives of other groups of herbicidally or growth-regulatory active ingredients. Suitable components in mixtures are, for example, 1,2,4-thiadiazoles, 1,3,4-thiadiazoles, amides, aminophosphoric acid and its derivatives, aminotriazoles, anilides, aryloxy-/hetaryloxyalkanic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-CF$_3$-phenylderivatives, carbamates, quinolinecarboxylic acid and its derivatives, chloracetanilides, cyclohexane-1,3-dione derivatives, diazines, dichloropropionic acid and its derivatives, dihydrobenzofuranes, dihydrofuran-3-ones, dinitroanilines, dinitrophenoles, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazole carboxamides and uracils.

Moreover, it may be advantageous to apply the compounds I, alone or in combination with other herbicides, in the form of a mixture with additional other crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates can also be added.

PREPARATION EXAMPLES

Example 1

Diethyl 1-chloro-2-(2-chloro-5-(3-chloro-5-trifluoromethylpyrid-2-yl)-4-fluorophenyl) ethylphosphonate (No. Iγ.3)

3 g (9 mmol) of 2-chloro-5-(3-chloro-5-trifluoromethylpyrid-2-yl)-4-fluoroaniline were added to a solution of 30.3 g (0.19 mol) of diethyl vinylphosphonate, 1.4 g of copper(II) chloride (10 mmol) and 1 g (10 mmol) of tert-butyl nitrite in 150 ml of acetonitrile. After 3 hours, 200 ml of methyl tert-butyl ether were added to the reaction mixture. The organic phase was subsequently washed twice with water, then dried over magnesium sulfate and finally concentrated. The crude product was purified by column chromatography (eluent: hexane/ethyl acetate=4:1). Yield: 1.6 g.

Example 2

Diethyl 1-chloro-2-(2-chloro-5-(3-chloro-5-trifluoromethylpyrid-2-yl)-4-fluorophenyl) vinylphosphonate (No. IIγ.3)

3 ml of butyllithium solution (1.5M in hexane; 4.5 mmol) were added to a solution, cooled to (−70)°C., of 2.3 g (9 mmol) of diethyl trichloromethanephosphonate in 30 ml of tetrahydrofuran in such a way that the temperature did not rise above (−65)°C. Stirring of the mixture was then continued for 1 hour at (−65) to (−70)°C., whereupon a solution of 1 g (3 mmol) of 2-chloro-5-(3-chloro-5-trifluoromethylpyrid-2-yl)-4-fluorobenzaldehyde in 20 ml of tetrahydrofuran was slowly added dropwise. After the mixture had been stirred for a further 30 minutes, the cooling bath was removed and the mixture was allowed to come to room temperature. The reaction solution was subsequently washed with saturated aqueous sodium chloride solution, then dried over magnesium sulfate and finally concentrated. The crude product was purified by column chromatography on silica gel (eluent: hexane/ethyl acetate=4:1). Yield: 0.8 g.

Example 3

Dimethyl 1-bromo-2-[2-chloro-5-(3-chloro-5-trifluoromethylpyrid-2-yl)phenyl]ethylphosphonate (No. Idα.2)

By following a method similar to the one described for Example 1 and using 32.6 g (0.24 mol) of dimethyl vinylphosphonate, 3.13 g (14 mmol) of copper(II) bromide, 1.33 g (13 mmol) of tert-butyl nitrite and 3.6 g (12 mmol) of 2-chloro-5-(3-chloro-5-trifluoromethylpyrid-2-yl)aniline, 1.2 g of the desired product of value were obtained.

Example 4

Diethyl 2-chloro-5-(3-chloro-5-trifluoromethylpyrid-2-yl)benzyloxymethylphosphonate (No. Inα.3)

To a solution of 0.66 g (3.9 mmol) of diethyl hydroxymethylphosphonate in 30 ml of tetrahydrofuran there were added 0.1 g (3.6 mmol) of sodium hydride and, after the mixture had been stirred for 15 minutes, 1 g (2.6 mmol) of 2-chloro-5-(3-chloro-5-trifluoromethylpyrid-2-yl)benzyl bromide. The mixture was subsequently stirred for 16 hours. The reaction mixture was then concentrated. The crude product obtained was purified by means of silica gel chromatography (eluent: hexane/ethyl acetate=1:1). Yield: 0.8 g.

Example 5

Diethyl 2-chloro-5-(3-chloro-5-trifluoromethylpyrid-2-yl)-4-fluorophenoxymethylphosphonate (No. Ioγ.3)

0.14 g (0.78 mmol) of bromine was added to a solution of 0.3 g (0.78 mmol) of 3-chloro-2-[4-chloro-2-fluoro-5-(methylthiomethoxy)phenyl]-5-trifluoromethylpyrid in 10 ml of tetrachloromethane. After the mixture had been stirred for 2 hours, it was concentrated. The residue was treated with 20 ml of triethyl phosphite. Stirring was subsequently continued for 16 hours, whereupon excess phosphite was removed under a high vacuum. Yield: 0.2 g.

Precursor 5.1

3-Chloro-2-[4-chloro-2-fluoro-5-(methylthiomethoxy) phenyl]-5-trifluoromethylpyridine 0.1 g (4.4 mmol) of sodium hydride was added to a solution of 1.3 g (4 mmol) of 2-chloro-5-(3-chloro-5-trifluoromethylpyrid-2-yl)-4-fluorophenol in 50 ml of dimethylformamide. After the mixture has been stirred for 1 hour, it was treated with 0.5 g (5.2 mmol) of methylthiomethyl chloride. Then, the mixture was stirred for another hour. For working-up, the reaction mixture was treated with 50 ml of water. The product was then extracted with 100 ml of methyl tert-butyl ether. The organic phase was dried over magnesium sulfate and finally concentrated. Yield: 0.3 g.

$^1$H NMR (270 MHz, in CDCl$_3$): δ [ppm]=2.31 (s, 3H), 5.24 (s, 2H), 7.12 (d, 1H), 7.30 (d, 1H), 8.08 (s, 1H), 8.88 (s, 1H).

Example 6

Diethyl 2-chloro-5-(3-chloro-5-trifluoromethylpyrid-2-yl)benzylphosphonate (No. Iaα.3)

A solution of 1 g (2.6 mmol) of 2-chloro-5-(3-chloro-5-trifluoromethylpyrid-2-yl)benzyl bromide in 10 ml of triethyl phosphite was heated for 12 hours at 80° to 90° C., whereupon excess triethyl phosphite was distilled off under a high vacuum. Yield: 1.1 g.

Example 7

1-Chloro-2-[2-chloro-5-(3-chloro-5-trifluoromethylpyrid-2-yl)-4-fluorophenyl]ethylphosphonic acid (No. Icγ.1)

0.7 g (4.2 mmol) of potassium iodide and 0.46 g (4.2 mmol) of chlorotrimethylsilane were added to a solution of 0.7 g (1.4 mol) of diethyl 1-chloro-2-[2-chloro-5-(3-chloro-5-trifluoromethylpyrid-2-yl)-4-fluorophenyl] ethylphosphonate in 20 ml of acetonitrile. The mixture was then heated for 4 hours at 50° to 60° C. whereupon it was concentrated. 20 ml of water and 50 ml of ethyl acetate were added to the residue. The organic phase was separated off, dried over magnesium sulfate and finally concentrated. Yield: quantitative.

Example 8

Diethyl 1-cyano-2-[2-chloro-5-(3-chloro-5-trifluoromethylpyrid-2-yl)phenyl]ethylphosphonate (No. Ifα.3)

2.27 ml (3.6 mmol) of 1.6M butyllithium solution in n-hexane were added to a solution, cooled to (−78)°C., of 0.69 g (3.89 mmol) of diethyl cyanomethylphosphonate in 50 ml of tetrahydrofuran. After the mixture had been stirred for 1 hour, it was treated with 1 g (2.6 mmol) of 2-chloro-5-(3-chloro-5-trifluoromethylpyrid-2-yl)benzyl bromide, dissolved in 10 ml of tetrahydrofuran. The mixture was then stirred for another 16 hours at approximately 20° C. It was then concentrated, and the residue which remained was treated with 50 ml of ethyl acetate. The product-containing organic phase was separated off, washed with water and saturated aqueous sodium chloride solution, dried over magnesium sulfate and finally concentrated. The crude product was purified by means of silica gel chromatography (eluent: hexane/ethyl acetate=4:1). Yield: 0.6 g.

Example 9

Diethyl 1-chloro-2-[2-chloro-5-(3-chloro-5-trifluoromethylpyrid-2-yl)phenyl]vinylphosphonate (No. IIα.3)

By following a method similar to Example 2 and using 33.7 g (0.13 mol) of diethyl trichloromethanephosphante, 41 ml of a butyllithium solution (1.6M in n-hexane; 63 mmol n-butyllithium) and 8.3 g (26 mmol) of 2-chloro-5-(3-chloro-5-trifluoromethylpyrid-2-yl)-benzaldehyde, 10 g of the desired product of value were obtained.

Example 10

1-Chloro-2-[2-chloro-5-(3-chloro-5-trifluoromethylpyrid-2yl)-phenyl]vinylphosphonic acid (No. IIα.1)

By following a method similar to the one described for Example 7 and using 4 g (8.1 mmol) of diethyl 1-chloro-2-[2-chloro-5-(3-chloro-5-trifluoromethylpyrid-2-yl)phenyl] vinylphosphonate, 4 g (24 mmol) of potassium iodide and 2.7 g (24 mmol) of chlorotrimethylsilane, 3 g of the desired product of value were obtained.

Example 11

Diallyl 1-chloro-2-[2-chloro-5-(3-chloro-5-trifluoromethylpyrid-2-yl) phenyl]vinylphosphonate (No. IIα.32)

0.9 g (7 mmol) of oxalyl chloride was added to a solution of 1 g (2.3 mmol) of 1-chloro-2-[2-chloro-5-(3-chloro-5-trifluoromethylpyrid-2-yl)phenyl]vinylphosphonic acid in 15 ml of 1,2-dichloroethane. Then, the reaction mixture was heated briefly to reflux temperature and subsequently concentrated. The resulting acid chloride was dissolved in 50 ml of dichloromethane. After 0.55 g (6.3 mmol) of pyridine and 0.4 g (6.3 mmol) of allyl alcohol had been added, the mixture was stirred for a further 16 hours. The mixture was then treated with water. The organic phase was subsequently separated off, dried over magnesium sulfate and concentrated. The crude product was purified by means of silica gel chromatography (eluent: hexane/ethyl acetate=4:1). Yield: 0.2 g.

In addition to those described above, a further number of substituted 2-phenylpyridines which were, or can be, prepared by similar methods are listed in Table 2 below:

TABLE 2

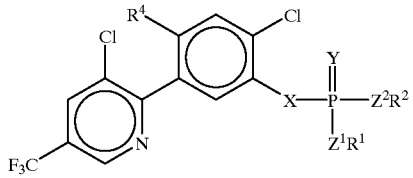

I {R³, R⁵ = Cl; R⁶ = CF₃; n = 0}

| No. | R⁴ | —X— | —P(=Y)(Z¹R¹)(Z²R²) | M.p./¹H NMR ($\delta$ in [ppm]), MS [m/z] |
|---|---|---|---|---|
| Iα. 3 | H | —CH₂— | —P(=O)(OC₂H₅)₂ | 1.27(t, 6H), 3.44(d, 2H), 4.09(quint., 4H), 7.51(d, 1H), 7.64(dd, 1H), 7.88(d, 1H), 8.03(d, 1H), 8.83(d, 1H) |
| Icα. 2 | H | —CH₂—CH(Cl)— | —P(=O)(OCH₃)₂ | 426[M—Cl]⁺ |
| Icα. 3 | H | —CH₂—CH(Cl)— | —P(=O)(OC₂H₅)₂ | 454[M—Cl]⁺ |
| Idα. 2 | H | —CH₂—CH(Br)— | —P(=O)(OCH₃)₂ | 504[M—H]⁺, 470[M—Cl]⁺ |
| Idα. 3 | H | —CH₂—CH(Br)— | —P(=O)(OC₂H₅)₂ | 1.38(t, 6H), 3.22(ddd, 1H), 3.82(ddd, 1H), 4.27(m, 5H), 7.52(d, 1H), 7.68(dd, 1H), 7.75(d, 1H), 8.08(s, 1H), 8.86(s, 1H) |
| Ifα. 3 | H | —CH₂—CH(CN)— | —P(=O)(OC₂H₅)₂ | 1.39(t, 3H), 1.43(t, 3H), 3.18(ddd, 1H), 3.42(ddd, 1H), 3.56(ddd, 1H), 4.30(m, 4H), 7.54(d, 1H), 7.73(dd, 1H), 7.83(d, 1H), 8.05(d, 1H), 8.85(d, 1H) |
| Icγ. 1 | F | —CH₂—CH(Cl)— | —P(=O)(OH)₂ | 3.12(ddd, 1H), 3.59(brd, 1H), 4.19(brt, 1H), 7.64(d, 1H), 7.68(d, 1H), 8.66(s, 1H), 9.10(s, 1H), 10.95(s, 2H) |
| Icγ. 2 | F | —CH₂—CH(Cl)— | —P(=O)(OCH₃)₂ | 3.14(ddd, 1H), 3.67(ddd, 1H), 3.88(d, 3H), 3.94(d, 3H), 4.26(dt, 1H), 7.29(d, 1H), 7.45(d, 1H), 8.07(s, 1H), 8.86(s, 1H) |
| Icγ. 3 | F | —CH₂—CH(Cl)— | —P(=O)(OC₂H₅)₂ | 1.39(t, 3H), 1.40(t, 3H), 3.12(dt, 1H), 3.70(ddd, 1H), 4.20–4.33(m, 5H), 7.29(d, 1H), 7.46(d, 1H), 8.08(s, 1H), 8.88(s, 1H) |
| Inα. 3 | H | —CH₂—OCH₂— | —P(=O)(OC₂H₅)₂ | 1.32(t, 6H), 3.90(d, 2H), 4.19(quint., 4H), 4.83(s, 2H), 7.50(d, 1H), 7.68(dd, 1H), 7.92(d, 1H), 8.07(s, 1H), 8.84(s, 1H) |
| IIα. 1 | H | —CH=C(Cl)— | —P(=O)(OH)₂ | resin |
| IIα. 3 | H | —CH=C(Cl)— | —P(=O)(OC₂H₅)₂ | 1.42(t, 6H), 4.24(m, 4H), 7.58(d, 1H), 7.77(dd, 1H), 7.96(d, 1H), 8.07(d, 1H), 8.32(d, 1H), 8.86(d, 1H) |
| IIα. 32 | H | —CH=C(Cl)— | —P(=O)(OCH₂—CH=CH₂)₂ | 4.67(m, 4H), 5.29(d, 2H), 5.43(d, 2H), 5.98(m, 2H), 7.58(d, 1H), 7.77(dd, 1H), 7.98(d, 1H), 8.06(d, 1H), 8.31(d, 1H), 8.86 d, 1H) |
| IIα. 36 | H | —CH=C(Cl)— | —P(=O)(OCH₂—C≡CH)₂ | 2.62(t, 2H), 4.84(dd, 4H), 7.59(d, 1H), 7.78(dd, 1H), 8.01(d, 1H), 8.06(d, 1H), 8.33(d, 1H), 8.86(d, 1H) |
| IIα. 38 | F | —CH=C(Cl)— | —P(=O)(OCH₂—CO—OCH₃)₂ | 3.82(s, 3H), 4.77(dd, 2H), 4.86(dd, 2H), 7.59(d, 1H), 7.78(dd, 1H), 8.06(d, 1H), 8.08(d, 1H), 8.36(d, 1H), 8.86(d, 1H) |
| IIα. 398 | H | —CH=C(Cl)— | —P(=O)[N(CH₃)—CH₂—CH₂—CH₂—N(CH₃)] | 1.92(m, 1H), 2.22(m, 1H), 2.72(d, 6H), 3.16(m, 2H), 3.39(m, 2H), 7.56(d, 1H), 7.72(dd, 1H), 7.87(d, 1H), 8.06(d, 1H), 8.23(d, 1H), 8.86(d, 1H) |

TABLE 2-continued

I {R³, R⁵ = Cl; R⁶ = CF₃; n = 0}

| No. | R⁴ | —X— | —P(=Y)(Z¹R¹)(Z²R²) | M.p./¹H NMR (δ in [ppm]), MS [m/z] |
|---|---|---|---|---|
| Iiγ. 3 | F | —CH=C(Cl)— | —P(=O)(OC₂H₅)₂ | 1.41(t, 6H), 4.15–4.30(m, 4H), 7.36(d, 1H), 7.91(d, 1H), 8.09(m, 2H), 8.89(S, 1H) |
| Ioγ. 3 | F | —OCH₂— | —P(=O)(OC₂H₅)₂ | 1.30(m, 6H), 4.00–4.30(m, 6H), 7.11(d, 1H), 7.15(dd, 1H), 8.06(s, 1H), 8.83(s, 1H) |

Use Examples (herbicidal activity)

The herbicidal action of the substituted 2-phenylpyridines I was demonstrated by the following greenhouse experiments:

The culture containers used were plastic flowerpots containing loamy sand with approximately 3.0% of humus as substrate. The seeds of the test plants were sown separately for each species.

For the pre-emergence treatment, the active ingredients, suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants unless this was adversely affected by the active ingredients.

For the post-emergence treatment, the test plants were grown to a plant height of from 3 to 15 cm, depending on the plant habit, and only then treated with the active ingredients which had been suspended or emulsified in water. To this end, the test plants were either sown directly and grown in the same containers, or they were first grown separately as seedlings and transplanted into the test containers a few days prior to treatment. The rate of application for the post-emergence treatment was 15.6, 7.8, 3.9 or 1.9 g/ha a.s. (active substance).

Depending on the species, the plants were kept at from 10°–25° C. and 20°–35° C., respectively. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage or normal course of growth.

The plants used in the greenhouse experiments belonged to the following species:

| Scientific Name | Common Name |
|---|---|
| Amaranthus retroflexus | redroot pigweed |
| Chenopodium album | lambsquarters (goose foot) |
| Galium aparine | catchweed bedstraw |
| Ipomoea subspecies | morningglory |
| Polygonum persicaria | lady's thumb |
| Solanum nigrum | black nightshade |

When rates of application of 3.9 and 1.9 g/ha a.s. were applied post-emergence, the compound No. Icγ.3 was very effective against the abovementioned plants.

When rates of 15.6 and 7.8 g/ha a.s. were applied, the compound No. Icγ.3 allowed a considerably better control of *Amaranthus retroflexus, Galium aparine, Ipomoea subspecies, Polygonum persicaria* and *Solanum nigrum* than the comparison compound A

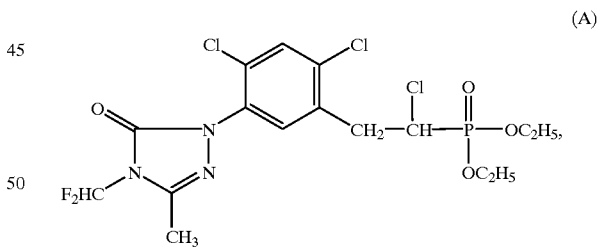

(A)

which is known from ACS Symp. Ser. 584, (1995), 90.

Use Examples (desiccant/defoliant activity)

The test plants used were young cotton plants with 4 leaves (without cotyledones) which had been grown under greenhouse conditions (relative atmospheric humidity 50 to 70%; day/night temperature 27°/20° C.).

The young cotton plants were subjected to foliar treatment with aqueous preparations of the active ingredients (with an addition of 0.15% by weight of the fatty alcohol alkoxylate Plurafac® LF 700¹), based on the spray mixture) until runoff point was reached. The amount of water applied was 1000 l/ha (converted). After 13 days, the number of leaves shed and the degree of defoliation in % were determined.

No leaves were shed in the untreated control plants.

We claim:

1. A 2-phenylpyridine of the formula I

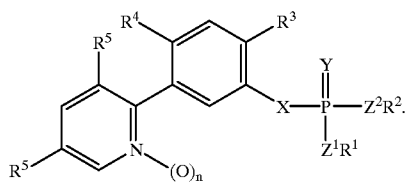

where the variables have the following meanings:

X is a chemical bond, 1,2-ethynediyl or
a methylene, 1,2-ethanediyl or 1,3-propylene bridge, which is unsubstituted or carries a hydroxyl, amino or $C_1$–$C_4$-alkylamino substituent;
methyleneoxymethylene, methylenethiamethylene, ethene-1,2-diyl, or
oxymethylene, thiamethylene, oxyethylene or thiaethylene, bonded to the phenyl ring via the hetero atom, the last two of these chains being unsubstituted or having hydroxyl, amino or $C_1$–$C_4$-alkylamino attached to the carbon atom adjacent to the phosphorus;
and where in each of the last mentioned 10 bridges is unsubstituted or carries one or two of the following substituents: cyano, carboxyl, halogen, $C_1$–$C_4$-alkyl, $C_1$–$C_4$-haloalkyl, $C_1$–$C_4$-alkoxy, $C_1$–$C_4$-haloalkoxy, ($C_1$–$C_4$-alkoxy)carbonyl and di-($C_1$–$C_4$-alkyl)amino;

Y is oxygen or sulfur;

$Z^1$ is oxygen, sulfur or —N($R^7$)—;

$Z^2$ is oxygen, sulfur or —N($R^8$)—;

$R^1$, $R^2$, $R^7$ and $R^8$ independently of one another are hydrogen, $C_1$–$C_6$-alkyl, $C_1$–$C_6$-haloalkyl, hydroxy-$C_1$–$C_4$-alkyl, cyano-$C_1$–$C_4$-alkyl, $C_1$–$C_4$-alkoxy-$C_1$–$C_4$-alkyl, $C_1$–$C_4$-haloalkoxy-$C_1$–$C_4$-alkyl, $C_3$–$C_4$-alkenyloxy-$C_1$–$C_4$-alkyl, $C_3$–$C_4$-alkynyloxy-$C_1$–$C_4$-alkyl, $C_3$–$C_8$-cycloalkoxy-$C_1$–$C_4$-alkyl, amino-$C_1$–$C_4$-alkyl, $C_1$–$C_4$-alkylamino-$C_1$–$C_4$-alkyl, di($C_1$–$C_4$-alkyl)amino-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_3$–$C_4$-alkenylthio-$C_1$–$C_4$-alkyl, $C_3$–$C_4$-alkynylthio-$C_1$–$C_4$-alkyl, $C_1$–$C_4$-alkylsulfinyl-$C_1$–$C_4$-alkyl, $C_1$–$C_4$-haloalkylsulfinyl-$C_1$–$C_4$-alkyl, $C_3$–$C_4$-alkenylsulfinyl-$C_1$–$C_4$-alkyl, $C_3$–$C_4$-alkynyl-sulfinyl-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, $C_3$–$C_4$-alkenylsulfonyl-$C_1$–$C_4$-alkyl, $C_3$–$C_4$-alkynylsulfonyl-$C_1$–$C_4$-alkyl, $C_3$–$C_6$-alkenyl, $C_3$–$C_6$-haloalkenyl, cyano-$C_3$–$C_6$-alkenyl, $C_3$–$C_6$-alkynyl, $C_3$–$C_6$-haloalkynyl, cyano-$C_3$–$C_6$-alkynyl, hydroxycarbonyl-$C_1$–$C_4$-alkyl, ($C_1$–$C_4$-alkoxy)carbonyl-$C_1$–$C_4$-alkyl, ($C_1$–$C_4$-alkyl-thio)carbonyl-$C_1$–$C_4$-alkyl, aminocarbonyl-$C_1$–$C_4$-alkyl, ($C_1$–$C_4$-alkyl)aminocarbonyl-$C_1$–$C_4$-alkyl, di($C_1$–$C_4$-alkyl)aminocarbonyl-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl or 3- to 7-membered heterocyclyl or heterocyclyl-$C_1$–$C_4$-alkyl, wherein the heterocyclyl moieties consist of carbon ring members and from one to three heteroatoms as ring members, said heteroatoms being selected from a group consisting of one to three nitrogen atoms, two oxygen atoms and two sulfur atoms, and wherein one carbon ring member optionally forms a carbonyl or a thiocarbonyl group, and wherein the heterocyclyl moieties are saturated, partially unsaturated or aromatic, wherein the cycloalkyl, the phenyl and the heterocyclyl rings are unsubstituted or carry one to four substituents selected from the group consisting of halogen, cyano, nitro, amino, hydroxyl, carboxyl, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkyl)carbonyl, ($C_1$–$C_4$-haloalkyl)carbonyl, ($C_1$–$C_4$-alkoxy)carbonyl, ($C_1$–$C_4$-alkyl)carbonyloxy, ($C_1$–$C_4$-haloalkyl)carbonyloxy and di($C_1$–$C_4$-alkyl)amino, or $R^1$ and $R^2$ $R^7$, or $R^2$ and $R^8$ together form a 1,2-ethanediyl, 1,3-propylene, tetramethylene, pentamethylene or ethyleneoxyethylene chain which is unsubstituted or carries one to four $C_1$–$C_4$-alkyl and/or one or two ($C_1$–$C_4$-alkoxy)carbonyl groups, or $R^1$ and $R^2$ together are 1,2-phenylene which is unsubstituted or carries one to three substituents selected from the group consisting of cyano, nitro, halogen, $C_1$–$C_4$-alkyl, $C_1$–$C_4$-haloalkyl, $C_1$–$C_4$-alkoxy and $C_1$–$C_4$-haloalkoxy;

$R^3$ is cyano, halogen, alkyl, $C_1$–$C_4$-haloalkyl, $C_1$–$C_4$-alkoxy or $C_1$–$C_4$-haloalkoxy;

$R^4$, $R^5$ in each case are hydrogen or halogen;

$R^6$ is halogen or $C_1$–$C_4$-haloalkyl;

n is zero or one;

or an agriculturally useful salt of a compound I.

2. A herbicidal composition comprising a herbicidally effective amount of at least one 2-phenylpyridine of the formula I or the agriculturally useful salt of I, defined in claim 1, and at least one inert or solid carrier and optionally at least one surfactant.

3. A composition for the desiccation or defoliation of plants comprising an effective amount of at least one 2-phenylpyridine of the formula I or the agriculturally useful salt of I, defined in claim 1, and at least one inert liquid or solid carrier and optionally at least one surfactant.

4. A method of controlling undesirable vegetation, which comprises treating plants, their environment or seeds with an effective amount of at least one 2-phenylpyridine of the formula I or the agriculturally useful salt of I, defined in claim 1.

5. A method for the desiccation or defoliation of plants, which comprises treating the plants with an effective amount of at least one 2-phenylpyridine of the formula I or the agriculturally useful salt of I, defined in claim 1.

6. The method defined in claim 4, wherein the plant is cotton.

7. The 2-phenylpyridine of the formula I defined in claim 1, wherein X denotes $CH_2$, $CH_2$—$CH_2$, $CH_2$—CH (halogen), $CH_2$—CH(CN), $CH_2$—CH($CH_3$), $CH_2$—CH ($COOCH_3$), $CH_2$—O—$CH_2$, CH=CH, CH=C(halogen), CH=C(CN), CH=C($CH_3$), CH=C($COOCH_3$) or O—$CH_2$.

8. The 2-phenylpyridine of the formula I defined in claim 1, wherein X denotes $CH_2$—CH(halogen) or CH=C (halogen).

9. The 2-phenylpyridine of the formula I defined in claim 1, wherein Y denotes oxygen.

10. The 2-phenylpyridine of the formula I defined in claim 1, wherein one of $Z^1$ and $Z^2$ denotes oxygen.

11. The 2-phenylpyridine of the formula I defined in claim 1, wherein $Z^1$ and $Z^2$ denote oxygen.

12. The 2-phenylpyridine of the formula I defined in claim 1, wherein one of $R^1$ and $R^2$ or one of $R^7$ and $R^8$ denotes hydrogen, $C_1$–$C_6$-alkyl, $C_1$–$C_6$-haloalkyl, $C_3$–$C_6$-alkenyl, $C_3$–$C_6$-haloalkenyl, $C_3$–$C_6$-alkynyl, ($C_1$–$C_4$-alkoxy)carbonyl-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl, 3- to 7-membered heterocyclyl or heterocyclyl-$C_1$–$C_4$-alkyl, or wherein $R^1$ and $R^2$ or $R^7$, or $R^2$ and $R^8$ together form a 1,2-ehtanediyl- or 1,3-propylene group.

13. The 2-phenylpyridine of the formula I defined in claim 1, wherein one of $R^1$ and $R^2$ or one of $R^7$ and $R^8$ denotes hydrogen, $C_1$–$C_6$-alkyl, $C_3$–$C_6$-alkenyl, $C_3$–$C_6$-alkynyl, $C_3$–$C_8$-cycloalkyl, phenyl or phenyl-$C_1$–$C_4$-alkyl, or wherein $R^1$ and $R^2$ together form a 1,3-propylene group.

14. The 2-phenylpyridine of the formula I defined in claim 1, wherein $R^3$ denotes cyano or chlorine.

15. The 2-phenylpyridine of the formula I defined in claim 1, wherein $R^4$ denotes hydrogen or fluorine.

16. The 2-phenylpyridine of the formula I defined in claim 1, wherein $R^5$ denotes chlorine.

17. The 2-phenylpyridine of the formula I defined in claim 1, wherein $R^6$ denotes trifluoromethyl.

18. The 2-phenylpyridine of the formula I defined in claim 1, wherein n is zero.

19. The 2-phenylpyridine of the formula I defined in claim 1, wherein $R^3$ denotes cyano or chlorine and $R^4$ denotes hydrogen or fluorine.

20. The 2-phenylpyridine of the formula I defined in claim 1, wherein $R^5$ denotes chlorine and $R^6$ denotes trifluoromethyl.

* * * * *

UNITED STATES PATENT AND TRADEMARK OFFICE
CERTIFICATE OF CORRECTION

PATENT NO. : 6,100,218
DATED : August 8, 2000
INVENTOR(S) : Zagar et al.

It is certified that error appears in the above-identified patent and that said Letters Patent is hereby corrected as shown below:

Column 55, claim 1,
Line 27, "where in" should be -- wherein --.

Column 56, claim 1,
Line 14, "$R^2R^7$" should be -- $R^2$ or $R^7$ --.

Column 56, claim 6,
Line 52, "claim 4" should be -- claim 5 --.

Column 57, claim 12,
Line 12, "1,2-ehtanediyl-" should be -- 1,2-ethanediyl- --.

Signed and Sealed this

Twenty-fifth Day of December, 2001

Attest:

*Attesting Officer*

JAMES E. ROGAN
*Director of the United States Patent and Trademark Office*